(12) United States Patent
Noda et al.

(10) Patent No.: US 11,306,300 B2
(45) Date of Patent: Apr. 19, 2022

(54) MICROORGANISM CAPABLE OF DISPLAYING α-GALACTOSIDASE ON SURFACE LAYER THEREOF, AND USE THEREOF

(71) Applicants: Kansai Chemical Engineering Co., Ltd., Hyogo (JP); Bio-energy Corporation, Hyogo (JP)

(72) Inventors: Hideo Noda, Hyogo (JP); Shinji Hama, Hyogo (JP)

(73) Assignees: KANSAI CHEMICAL ENGINEERING CO., LTD., Hyogo (JP); BIO-ENERGY CORPORATION, Hyogo (JP)

( * ) Notice: Subject to any disclaimer, the term of this patent is extended or adjusted under 35 U.S.C. 154(b) by 210 days.

(21) Appl. No.: 16/607,768

(22) PCT Filed: May 10, 2018

(86) PCT No.: PCT/JP2018/018201
§ 371 (c)(1),
(2) Date: Oct. 24, 2019

(87) PCT Pub. No.: WO2018/207889
PCT Pub. Date: Nov. 15, 2018

(65) Prior Publication Data
US 2021/0284984 A1 Sep. 16, 2021

(30) Foreign Application Priority Data
May 11, 2017 (JP) .............................. JP2017-095097

(51) Int. Cl.
| C12N 9/40 | (2006.01) |
| C12N 15/81 | (2006.01) |
| C12P 7/06 | (2006.01) |
| C12P 7/56 | (2006.01) |
| C12P 19/02 | (2006.01) |
| C12P 19/14 | (2006.01) |

(52) U.S. Cl.
CPC .......... *C12N 9/2465* (2013.01); *C12N 15/81* (2013.01); *C12P 7/06* (2013.01); *C12P 7/56* (2013.01); *C12P 19/02* (2013.01); *C12P 19/14* (2013.01)

(58) Field of Classification Search
CPC ....... C12N 9/2465; C12N 15/81; C12P 19/14; C12P 7/06; C12P 7/56; C12P 19/02
See application file for complete search history.

(56) References Cited

U.S. PATENT DOCUMENTS

| 5,919,690 | A | 7/1999 | Knap et al. |
| 7,192,764 | B2 | 3/2007 | Fukuda et al. |
| 8,592,188 | B2 * | 11/2013 | Franklin .................. A23D 7/00 435/134 |
| 8,859,245 | B2 | 10/2014 | Uyama et al. |
| 9,580,729 | B2 * | 2/2017 | Noda ........................ C12P 7/14 |
| 9,816,113 | B2 | 11/2017 | Noda et al. |
| 10,654,902 | B2 * | 5/2020 | Scott ..................... C07K 14/245 |
| 2017/0218382 | A1 | 8/2017 | Kondo et al. |

FOREIGN PATENT DOCUMENTS

| CN | 102242094 A | 11/2011 |
| CN | 102242095 A | 11/2011 |
| JP | 08-508644 A | 9/1996 |
| JP | 11-290078 | 10/1999 |
| WO | 02/085935 A1 | 10/2002 |
| WO | 2007/114017 A1 | 10/2007 |
| WO | 2010101158 A1 | 9/2012 |
| WO | 2015/033948 A1 | 3/2015 |
| WO | 2016/017736 A1 | 2/2016 |

OTHER PUBLICATIONS

De Almada et al., Paraprobiotics: evidences on their ability to modify biological responses, inactivation methods and perspectives on their application in foods. Trends Food Sci. Technol., 2016, vol. 58: 96-114. (Year: 2016).*
Kisselev L., Polypeptide release factors in prokaryotes and eukaryotes: same function, different structure. Structure, 2002, vol. 10: 8-9. (Year: 2002).*
LeBlanc et al., Reduction of non-digestible oligosaccharides in soymilk: application of engineered lactic acid bacteria that produce a-galactosidase. Genetics Mol. Res., 2004, vol. 3(3): 432-440. (Year: 2004).*
Schreuder et al., Immobilizing proteins on the surface of the yeast. Tibtech., 1996, vol. 14: 115-120. (Year: 1996).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Nakai et al., Aspergillus nidulans a-galactosidase of glycoside hydrolase family 36 catalyses the formation of a-galacto-oligosaccharides by transglycosylation. FEBS Journal, 2010, vol. 277: 3538-3551. (Year: 2010).*
Wieeczorek A., Engineering Lactococcus lactis for the scaffold protein-mediated surface display of recombinant enzymes. Ph.D. Thesis, 2012, Concordia Univ., pp. 1-170 (Year: 2012).*

(Continued)

*Primary Examiner* — Ganapathirama Raghu
(74) *Attorney, Agent, or Firm* — Ajay A. Jagtiani; Miles & Stockbridge P.C.

(57) ABSTRACT

The present invention provides a transformed microorganism capable of displaying α-galactosidase on its surface layer. Also provided is a method for producing an alcohol, which includes the step of culturing the transformed microorganism in a culture medium containing a material that contains an oligosaccharide α-1,6 linked α-galactose. Also provided is a method for producing lactic acid using such a transformed microorganism together with a material that contains an oligosaccharide α-1,6 linked α-galactose. According to the present invention, a microorganism can be provided, which can degrade an oligosaccharide containing α-1,6 linked α-galactose, which may occur in soybean molasses.

12 Claims, 5 Drawing Sheets

Specification includes a Sequence Listing.

(56) References Cited

OTHER PUBLICATIONS

Wen et al., Yeast Surface Display of Trifunctional Minicellulosomes for Simultaneous Saccharification and Fermentation of Cellulose to Ethanol. appl. Environ. Micriol., 2010, vol. 76(4): 1251-1260. (Year: 2010).*
Eur. J. Biochem., 268, 2982-2990 (2001).
Biotechnology for Biofuels, 7(1):8 (2014).
Seibutsu-kogaku (Journal of the Society for Biotechnology, Japan), vol. 89,No. 4,154-160 (2011).
Proceedings of the Society of Chemical Engineers, Japan, 70th Annual Meeting, Session ID F123 (http://doi.org/10.11491/scej.2005.0.255.0).
Appl. Environ. Microbiol., 72(1), 269-275 (2006).
Appl. Environ. Microbiol., 74(4), 1117-1123 (2008).
Appl. Microbiol. Biotechnol., 81, 711-719 (2008).
Appl. Microbiol. Biotechnol., 84:733-739 (2009).
Reports of the Graduate School/Faculty of Engineering, Tottori University, vol. 47, 12-27 (2016).
Appl. Microbiol. Biotechnol., 2010, vol. 88, p. 87-94.
Process Biochem., 2006, vol. 41, p. 909-914.
Appl Microbiol Biotechnol, 2010, vol. 88, p. 381-388.
PLoS One. 2012; 7(5): e37226.
Appl. Environ. Microbiol. 2009, vol. 75, 462-467.
Appl. Microbiol. Biotechnol., 2011, vol. 92, 67-76.
PNAS, 2003, vol. 100, p. 1990-1995.
FEMS Microbiol. Lett., 2010, vol. 302, p. 8-14.
Appl Microbiol Biotechnol, 2016, vol. 100, p. 2449-2458.
Search Report and Written Opinion issued in PCT Application No. PCT/JP2018/018201.
Schreuder et al., "Targeting of Heterologous Protein to the Cell Wall of *Saccharomyces cerevisiae*" Yeast, vol. 9, pp. 399-409 (1993).
Hu et al., "Characterization of a Novel LysM Domain from Lactobacillus fermentum Bacteriophage Endolysin and its Ude as an Anchor to Display Heterologous Proteins on Surfaces of Lactic Acid Bacteria", Applied and Environmental Microbiology, vol. 76, No. 8, pp. 2410-2418 (2010).

* cited by examiner

SEQUENCE LISTING

```
<160> NUMBER OF SEQ ID NOS: 16

<210> SEQ ID NO 1
<211> LENGTH: 2181
<212> TYPE: DNA
<213> ORGANISM: Aspergillus oryzae
<220> FEATURE:
<221> NAME/KEY: CDS
<222> LOCATION: (1)..(2181)
<223> OTHER INFORMATION: XM_001827585.2 Aspergillus oryzae RIB40 alpha-
      galactosidase C

<400> SEQUENCE: 1 atg gcg cag gaa act tca agc aac aat gca gtt gtc gcg gac ggc aaa        48
Met Ala Gln Glu Thr Ser Ser Asn Asn Ala Val Val Ala Asp Gly Lys
1               5                   10                  15 aca ttt gct ctc aat gga gag aat gtc tca tac cgc ttc cga gtg aac        96
Thr Phe Ala Leu Asn Gly Glu Asn Val Ser Tyr Arg Phe Arg Val Asn
                20                  25                  30 gag acc acg ggt gac cta gtg tca gat cat ttc ggc ggc agt atc act       144
Glu Thr Thr Gly Asp Leu Val Ser Asp His Phe Gly Gly Ser Ile Thr
            35                  40                  45
```

-continued

| | | |
|---|---|---|
| ggc aat ctc ttc cca gga ttt ggt gcc gag gca ctt ggc ggc tgg gtt<br>Gly Asn Leu Phe Pro Gly Phe Gly Ala Glu Ala Leu Gly Gly Trp Val<br>50              55                  60 | | 192 |
| ggt ttg gca ggc cgt ttt cgc cgt gag ttt cca gat cac ggc cgg gga<br>Gly Leu Ala Gly Arg Phe Arg Arg Glu Phe Pro Asp His Gly Arg Gly<br>65              70                  75                  80 | | 240 |
| gat ttt cgg att ccc gcc gtt cgg att cgt caa gag gca ggc tac acc<br>Asp Phe Arg Ile Pro Ala Val Arg Ile Arg Gln Glu Ala Gly Tyr Thr<br>                85                  90                  95 | | 288 |
| gtg acg gat ctg cag tat cag tca tac tcg gtg att ccg gga aag cct<br>Val Thr Asp Leu Gln Tyr Gln Ser Tyr Ser Val Ile Pro Gly Lys Pro<br>            100                 105                 110 | | 336 |
| gct ttg ccc ggt ctg cct tca acc ttt ggc agt gaa gag gat gtc aca<br>Ala Leu Pro Gly Leu Pro Ser Thr Phe Gly Ser Glu Glu Asp Val Thr<br>            115                 120                 125 | | 384 |
| act ttg gtg gtt cat ctg tac gac aac tac agc tcc atc gct gtg gat<br>Thr Leu Val Val His Leu Tyr Asp Asn Tyr Ser Ser Ile Ala Val Asp<br>130             135                 140 | | 432 |
| ctg tcg tac tca atc ttc cct aaa tat gac gcc att gtg cgc agc gcg<br>Leu Ser Tyr Ser Ile Phe Pro Lys Tyr Asp Ala Ile Val Arg Ser Ala<br>145             150                 155                 160 | | 480 |
| aac gtt acg aac aag ggt act caa aat atc aca gtt gag gca ctg tcc<br>Asn Val Thr Asn Lys Gly Thr Gln Asn Ile Thr Val Glu Ala Leu Ser<br>                165                 170                 175 | | 528 |
| agc ttc agc ttc gat ttc cca tac gaa gat ctt gaa atg att agc ctc<br>Ser Phe Ser Phe Asp Phe Pro Tyr Glu Asp Leu Glu Met Ile Ser Leu<br>            180                 185                 190 | | 576 |
| agg ggc gac tgg gcg aga gaa gcc cac cgt cag agg cga aag gtg gaa<br>Arg Gly Asp Trp Ala Arg Glu Ala His Arg Gln Arg Arg Lys Val Glu<br>            195                 200                 205 | | 624 |
| tac gga ctc caa ggc ttc gga agt agc act ggt ttc tcc tct cac ctg<br>Tyr Gly Leu Gln Gly Phe Gly Ser Ser Thr Gly Phe Ser Ser His Leu<br>210             215                 220 | | 672 |
| cac aac ccc ttt ctt gcg ata gtg cat ccc tcc act acg gaa tct cag<br>His Asn Pro Phe Leu Ala Ile Val His Pro Ser Thr Thr Glu Ser Gln<br>225             230                 235                 240 | | 720 |
| ggt gag gcc tgg gga ttt aac ctt gtc tac aca ggc tcg ttc tcc gtt<br>Gly Glu Ala Trp Gly Phe Asn Leu Val Tyr Thr Gly Ser Phe Ser Val<br>                245                 250                 255 | | 768 |
| gat gtc gag aag ggc tcc cag ggc ctc act cgc gct ctg ctg gga ttc<br>Asp Val Glu Lys Gly Ser Gln Gly Leu Thr Arg Ala Leu Leu Gly Phe<br>            260                 265                 270 | | 816 |
| aat ccc agt cag ctg tct tgg cag ctg ggt gcg ggc gag aca ctt acc<br>Asn Pro Ser Gln Leu Ser Trp Gln Leu Gly Ala Gly Glu Thr Leu Thr<br>            275                 280                 285 | | 864 |
| tcg ccg gaa tgt gtt tca gtc tac tca agt gac ggc atc ggc ggc atg<br>Ser Pro Glu Cys Val Ser Val Tyr Ser Ser Asp Gly Ile Gly Gly Met<br>290             295                 300 | | 912 |
| tct cgt tca ttc cat cgc ctc tac cgc aac cac ctg atc aag agc aag<br>Ser Arg Ser Phe His Arg Leu Tyr Arg Asn His Leu Ile Lys Ser Lys<br>305             310                 315                 320 | | 960 |
| ttc gcc aca tcg gat cgc ccg ccg ctg ctg aac agc tgg gag ggt ctg<br>Phe Ala Thr Ser Asp Arg Pro Pro Leu Leu Asn Ser Trp Glu Gly Leu<br>                325                 330                 335 | | 1008 |
| tat ttc gac tac aat gag agc aca atc tac cgc ttg gct gag gag tcg<br>Tyr Phe Asp Tyr Asn Glu Ser Thr Ile Tyr Arg Leu Ala Glu Glu Ser<br>            340                 345                 350 | | 1056 |
| gcc gcc ttg gga gtg aaa ctg ttc gtt atg gac gac ggt tgg ttc ggc<br>Ala Ala Leu Gly Val Lys Leu Phe Val Met Asp Asp Gly Trp Phe Gly<br>            355                 360                 365 | | 1104 |

-continued

| | | |
|---|---|---|
| gac aag tac ccc cgt gta tcg gat aac gcc ggt ctg ggt gac tgg gtg<br>Asp Lys Tyr Pro Arg Val Ser Asp Asn Ala Gly Leu Gly Asp Trp Val<br>370 375 380 | | 1152 |
| cct aac ccg gac cgc ttt cct gat ggc cta acc ccc ctg gtg gaa gat<br>Pro Asn Pro Asp Arg Phe Pro Asp Gly Leu Thr Pro Leu Val Glu Asp<br>385 390 395 400 | | 1200 |
| gtc acg aag ctg aag gca gga aac tcc tca acc gac ctc cgc ttt ggc<br>Val Thr Lys Leu Lys Ala Gly Asn Ser Ser Thr Asp Leu Arg Phe Gly<br>405 410 415 | | 1248 |
| ctc tgg gtt gaa cca gaa atg gcc aac ccc aac tcg acc ctg tac cat<br>Leu Trp Val Glu Pro Glu Met Ala Asn Pro Asn Ser Thr Leu Tyr His<br>420 425 430 | | 1296 |
| gag cac cct gac tgg gtg ctt cat gcc ggc caa tac cca cgc acc ttg<br>Glu His Pro Asp Trp Val Leu His Ala Gly Gln Tyr Pro Arg Thr Leu<br>435 440 445 | | 1344 |
| caa cgc aac cag ctc gtg ctc aac ctt gct ttg cct gag gtg cag gac<br>Gln Arg Asn Gln Leu Val Leu Asn Leu Ala Leu Pro Glu Val Gln Asp<br>450 455 460 | | 1392 |
| tat atc atc gat gag att acc aac atc ctc aac agc tcg gct att tcc<br>Tyr Ile Ile Asp Glu Ile Thr Asn Ile Leu Asn Ser Ser Ala Ile Ser<br>465 470 475 480 | | 1440 |
| tat gtg aag tgg gac ttc aac cgg gcg atg cac gag aca ccc tcc ccc<br>Tyr Val Lys Trp Asp Phe Asn Arg Ala Met His Glu Thr Pro Ser Pro<br>485 490 495 | | 1488 |
| agc aac gac cac gaa tac atc ctg ggc atg tac cgg gtg ttc gac acc<br>Ser Asn Asp His Glu Tyr Ile Leu Gly Met Tyr Arg Val Phe Asp Thr<br>500 505 510 | | 1536 |
| ctg acc acg cgc ttc ccc gat gtt ctg tgg gaa ggt tgt gcc tct ggt<br>Leu Thr Thr Arg Phe Pro Asp Val Leu Trp Glu Gly Cys Ala Ser Gly<br>515 520 525 | | 1584 |
| ggt gga cgt ttc gac ccc ggt gta ctt gag tac ttc ccg cag atc tgg<br>Gly Gly Arg Phe Asp Pro Gly Val Leu Glu Tyr Phe Pro Gln Ile Trp<br>530 535 540 | | 1632 |
| acc tcc gac aac acc gat gcc ctg atg cgc atc acc atc cag cta ggt<br>Thr Ser Asp Asn Thr Asp Ala Leu Met Arg Ile Thr Ile Gln Leu Gly<br>545 550 555 560 | | 1680 |
| act tca ctg gca tac cct ccg agc gcc atg ggt gcc cat ctc tca gca<br>Thr Ser Leu Ala Tyr Pro Pro Ser Ala Met Gly Ala His Leu Ser Ala<br>565 570 575 | | 1728 |
| gtc ccg aat gcc cag act gga cgt acc att cct gtc aaa ttc cgt ggc<br>Val Pro Asn Ala Gln Thr Gly Arg Thr Ile Pro Val Lys Phe Arg Gly<br>580 585 590 | | 1776 |
| cac gtc gcc atg atg ggc gga tca ttc ggt ctc gaa cta gac ccc gcc<br>His Val Ala Met Met Gly Gly Ser Phe Gly Leu Glu Leu Asp Pro Ala<br>595 600 605 | | 1824 |
| gag ctg cag gag gat gag aag gcc gaa gtc ccg gga ctg att gcc ctt<br>Glu Leu Gln Glu Asp Glu Lys Ala Glu Val Pro Gly Leu Ile Ala Leu<br>610 615 620 | | 1872 |
| gca gaa aag gtt aac ccg atc atc ctg act ggc gat atg tgg cgt ctc<br>Ala Glu Lys Val Asn Pro Ile Ile Leu Thr Gly Asp Met Trp Arg Leu<br>625 630 635 640 | | 1920 |
| agg ctt ccc gag gag tct aac tgg ccg gcg gtg cta ttc atc tct gag<br>Arg Leu Pro Glu Glu Ser Asn Trp Pro Ala Val Leu Phe Ile Ser Glu<br>645 650 655 | | 1968 |
| gat ggt aac caa gct gtc ctc ttc tac ttc cag ctc ggc cct aat gtt<br>Asp Gly Asn Gln Ala Val Leu Phe Tyr Phe Gln Leu Gly Pro Asn Val<br>660 665 670 | | 2016 |
| aac cat gcc act ccc tgg ctc agg ctg cag gga ttg gat cct aag gcc<br>Asn His Ala Thr Pro Trp Leu Arg Leu Gln Gly Leu Asp Pro Lys Ala<br>675 680 685 | | 2064 |

| | | | | | | | | | | | | | | |
|---|---|---|---|---|---|---|---|---|---|---|---|---|---|---|
| acg | tat | agc | gtt | gat | gga | aac | gga | tcg | tac | tct | ggt | gcg | aca | ttg | atg | 2112 |
| Thr | Tyr | Ser | Val | Asp | Gly | Asn | Gly | Ser | Tyr | Ser | Gly | Ala | Thr | Leu | Met | |
| | | 690 | | | | 695 | | | | 700 | | | | | | |

| | | | | | | | | | | | | | | |
|---|---|---|---|---|---|---|---|---|---|---|---|---|---|---|
| aac | atg | gga | ctg | cag | tac | aag | ttt | gaa | tcg | gat | tat | gat | agc | aag | gtg | 2160 |
| Asn | Met | Gly | Leu | Gln | Tyr | Lys | Phe | Glu | Ser | Asp | Tyr | Asp | Ser | Lys | Val | |
| 705 | | | | 710 | | | | | 715 | | | | | 720 | | |

| | | | | | |
|---|---|---|---|---|---|
| gtg | ttc | ttg | cag | aag | cag | tga | 2181 |
| Val | Phe | Leu | Gln | Lys | Gln | | |
| | | | 725 | | | | |

<210> SEQ ID NO 2
<211> LENGTH: 726
<212> TYPE: PRT
<213> ORGANISM: Aspergillus oryzae

<400> SEQUENCE: 2

Met Ala Gln Glu Thr Ser Ser Asn Asn Ala Val Val Ala Asp Gly Lys
1               5                   10                  15

Thr Phe Ala Leu Asn Gly Glu Asn Val Ser Tyr Arg Phe Arg Val Asn
            20                  25                  30

Glu Thr Thr Gly Asp Leu Val Ser Asp His Phe Gly Gly Ser Ile Thr
        35                  40                  45

Gly Asn Leu Phe Pro Gly Phe Gly Ala Glu Ala Leu Gly Gly Trp Val
    50                  55                  60

Gly Leu Ala Gly Arg Phe Arg Arg Glu Phe Pro Asp His Gly Arg Gly
65                  70                  75                  80

Asp Phe Arg Ile Pro Ala Val Arg Ile Arg Gln Glu Ala Gly Tyr Thr
                85                  90                  95

Val Thr Asp Leu Gln Tyr Gln Ser Tyr Ser Val Ile Pro Gly Lys Pro
            100                 105                 110

Ala Leu Pro Gly Leu Pro Ser Thr Phe Gly Ser Glu Glu Asp Val Thr
        115                 120                 125

Thr Leu Val Val His Leu Tyr Asp Asn Tyr Ser Ser Ile Ala Val Asp
    130                 135                 140

Leu Ser Tyr Ser Ile Phe Pro Lys Tyr Asp Ala Ile Val Arg Ser Ala
145                 150                 155                 160

Asn Val Thr Asn Lys Gly Thr Gln Asn Ile Thr Val Glu Ala Leu Ser
                165                 170                 175

Ser Phe Ser Phe Asp Phe Pro Tyr Glu Asp Leu Glu Met Ile Ser Leu
            180                 185                 190

Arg Gly Asp Trp Ala Arg Glu Ala His Arg Gln Arg Lys Val Glu
        195                 200                 205

Tyr Gly Leu Gln Gly Phe Gly Ser Ser Thr Gly Phe Ser Ser His Leu
    210                 215                 220

His Asn Pro Phe Leu Ala Ile Val His Pro Ser Thr Thr Glu Ser Gln
225                 230                 235                 240

Gly Glu Ala Trp Gly Phe Asn Leu Val Tyr Thr Gly Ser Phe Ser Val
                245                 250                 255

Asp Val Glu Lys Gly Ser Gln Gly Leu Thr Arg Ala Leu Leu Gly Phe
            260                 265                 270

Asn Pro Ser Gln Leu Ser Trp Gln Leu Gly Ala Gly Glu Thr Leu Thr
        275                 280                 285

Ser Pro Glu Cys Val Ser Val Tyr Ser Ser Asp Gly Ile Gly Gly Met
    290                 295                 300

Ser Arg Ser Phe His Arg Leu Tyr Arg Asn His Leu Ile Lys Ser Lys
305                 310                 315                 320

-continued

Phe Ala Thr Ser Asp Arg Pro Pro Leu Leu Asn Ser Trp Glu Gly Leu
                325                 330                 335

Tyr Phe Asp Tyr Asn Glu Ser Thr Ile Tyr Arg Leu Ala Glu Glu Ser
                340                 345                 350

Ala Ala Leu Gly Val Lys Leu Phe Val Met Asp Asp Gly Trp Phe Gly
                355                 360                 365

Asp Lys Tyr Pro Arg Val Ser Asp Asn Ala Gly Leu Gly Asp Trp Val
                370                 375                 380

Pro Asn Pro Asp Arg Phe Pro Asp Gly Leu Thr Pro Leu Val Glu Asp
385                 390                 395                 400

Val Thr Lys Leu Lys Ala Gly Asn Ser Ser Thr Asp Leu Arg Phe Gly
                405                 410                 415

Leu Trp Val Glu Pro Glu Met Ala Asn Pro Asn Ser Thr Leu Tyr His
                420                 425                 430

Glu His Pro Asp Trp Val Leu His Ala Gly Gln Tyr Pro Arg Thr Leu
                435                 440                 445

Gln Arg Asn Gln Leu Val Leu Asn Leu Ala Leu Pro Glu Val Gln Asp
                450                 455                 460

Tyr Ile Ile Asp Glu Ile Thr Asn Ile Leu Asn Ser Ser Ala Ile Ser
465                 470                 475                 480

Tyr Val Lys Trp Asp Phe Asn Arg Ala Met His Glu Thr Pro Ser Pro
                485                 490                 495

Ser Asn Asp His Glu Tyr Ile Leu Gly Met Tyr Arg Val Phe Asp Thr
                500                 505                 510

Leu Thr Thr Arg Phe Pro Asp Val Leu Trp Glu Gly Cys Ala Ser Gly
                515                 520                 525

Gly Gly Arg Phe Asp Pro Gly Val Leu Glu Tyr Phe Pro Gln Ile Trp
                530                 535                 540

Thr Ser Asp Asn Thr Asp Ala Leu Met Arg Ile Thr Ile Gln Leu Gly
545                 550                 555                 560

Thr Ser Leu Ala Tyr Pro Pro Ser Ala Met Gly Ala His Leu Ser Ala
                565                 570                 575

Val Pro Asn Ala Gln Thr Gly Arg Thr Ile Pro Val Lys Phe Arg Gly
                580                 585                 590

His Val Ala Met Met Gly Gly Ser Phe Gly Leu Glu Leu Asp Pro Ala
                595                 600                 605

Glu Leu Gln Glu Asp Glu Lys Ala Glu Val Pro Gly Leu Ile Ala Leu
                610                 615                 620

Ala Glu Lys Val Asn Pro Ile Ile Leu Thr Gly Asp Met Trp Arg Leu
625                 630                 635                 640

Arg Leu Pro Glu Glu Ser Asn Trp Pro Ala Val Leu Phe Ile Ser Glu
                645                 650                 655

Asp Gly Asn Gln Ala Val Leu Phe Tyr Phe Gln Leu Gly Pro Asn Val
                660                 665                 670

Asn His Ala Thr Pro Trp Leu Arg Leu Gln Gly Leu Asp Pro Lys Ala
                675                 680                 685

Thr Tyr Ser Val Asp Gly Asn Gly Ser Tyr Ser Gly Ala Thr Leu Met
                690                 695                 700

Asn Met Gly Leu Gln Tyr Lys Phe Glu Ser Asp Tyr Asp Ser Lys Val
705                 710                 715                 720

Val Phe Leu Gln Lys Gln
                725

```
<210> SEQ ID NO 3
<211> LENGTH: 22
<212> TYPE: DNA
<213> ORGANISM: Artificial Sequence
<220> FEATURE:
<223> OTHER INFORMATION: Fw primer for AOAglC

<400> SEQUENCE: 3
atgttcggct ctccaaagcg tg                                                22

<210> SEQ ID NO 4
<211> LENGTH: 21
<212> TYPE: DNA
<213> ORGANISM: Artificial Sequence
<220> FEATURE:
<223> OTHER INFORMATION: Rv primer for AOAglC

<400> SEQUENCE: 4
tcactgcttc tgcaagaaca c                                                 21

<210> SEQ ID NO 5
<211> LENGTH: 799
<212> TYPE: DNA
<213> ORGANISM: Saccharomyces cerevisiae
<220> FEATURE:
<221> NAME/KEY: misc_feature
<222> LOCATION: (1)..(799)
<223> OTHER INFORMATION: SED1 promoter

<400> SEQUENCE: 5
attggatata gaaaattaac gtaaggcagt atcttttcac aatgtacttg caacgcggcg       60
acttaaagtt gaagtacaac ctgcagcagc ggcttttgt acggtacgcc aaactgtcaa      120
tggataatat tgcgtagacc gaaaaaggta atcctcaaca ctacccgtgg tggatgacct      180
aaagcagtaa tattggttgg aattatctcc cagacggcac cgtctcccccg agaaagctta    240 gccccgaggt ctaccttcca tacaccactg attgctccac gtcatgcggc cttctttcga     300
ggacaaaaag gcatatatcg ctaaaattag ccatcagaac cgttattgtt attatatttt     360
cattacgaaa gaggagaggg cccagcgcgc cagacacaca cggtcattga ttactttatt     420
tggctaaaga tccatccctt ctcgatgtca tctctttcca ttcttgtgta tttttgattg     480
aaaatgattt tttgtccact aatttctaaa ataagacaa aaagcctta agcagttttt      540 catccatttt actacggtaa aatgaattag tacggtatgg ctcccagtcg cattattttt     600
agattggccg taggggctgg ggtagaacta gagtaaggaa cattgctctg ccctcttttg     660
aactgtcata taaatacctg acctatttta ttctccatta tcgtattatc tcacctctct     720
ttttctattc tcttgtaatt attgatttat agtcgtaact acaaagacaa gcaaataaa      780 atacgttcgc tctattaag                                                   799

<210> SEQ ID NO 6
<211> LENGTH: 75
<212> TYPE: DNA
<213> ORGANISM: Rhizopus oryzae
<220> FEATURE:
<221> NAME/KEY: CDS
<222> LOCATION: (1)..(75)
<223> OTHER INFORMATION: Glucoamylase secresion signal
```

-continued

<400> SEQUENCE: 6

```
atg caa ctg ttc aat ttg cca ttg aaa gtt tca ttc ttt ctc gtc ctc    48
Met Gln Leu Phe Asn Leu Pro Leu Lys Val Ser Phe Phe Leu Val Leu
1               5                   10                  15 tct tac ttt tct ttg ctc gtt tct gct                                75
Ser Tyr Phe Ser Leu Leu Val Ser Ala
            20                  25
```

<210> SEQ ID NO 7
<211> LENGTH: 25
<212> TYPE: PRT
<213> ORGANISM: Rhizopus oryzae

<400> SEQUENCE: 7

```
Met Gln Leu Phe Asn Leu Pro Leu Lys Val Ser Phe Phe Leu Val Leu
1               5                   10                  15

Ser Tyr Phe Ser Leu Leu Val Ser Ala
            20                  25
```

<210> SEQ ID NO 8
<211> LENGTH: 2172
<212> TYPE: DNA
<213> ORGANISM: Aspergillus oryzae
<220> FEATURE:
<221> NAME/KEY: CDS
<222> LOCATION: (1)..(2172)
<223> OTHER INFORMATION: Aspergillus oryzae RIB40 alpha-galactosidase C
      in pAUR101

<400> SEQUENCE: 8

```
cag gaa act tca agc aac aat gca gtt gtc gcg gac ggc aaa aca ttt    48
Gln Glu Thr Ser Ser Asn Asn Ala Val Val Ala Asp Gly Lys Thr Phe
1               5                   10                  15 gct ctc aat gga gag aat gtc tca tac cgc ttc cga gtg aac gag acc    96
Ala Leu Asn Gly Glu Asn Val Ser Tyr Arg Phe Arg Val Asn Glu Thr
            20                  25                  30 acg ggt gac cta gtg tca gat cat ttc ggc ggc agt atc act ggc aat   144
Thr Gly Asp Leu Val Ser Asp His Phe Gly Gly Ser Ile Thr Gly Asn
        35                  40                  45 ctc ttc cca gga ttt ggt gcc gag gca ctt ggc ggc tgg gtt ggt ttg   192
Leu Phe Pro Gly Phe Gly Ala Glu Ala Leu Gly Gly Trp Val Gly Leu
    50                  55                  60 gca ggc cgt ttt cgc cgt gag ttt cca gat cac ggc cgg gga gat ttt   240
Ala Gly Arg Phe Arg Arg Glu Phe Pro Asp His Gly Arg Gly Asp Phe
65                  70                  75                  80 cgg att ccc gcc gtt cgg att cgt caa gag gca ggc tac acc gtg acg   288
Arg Ile Pro Ala Val Arg Ile Arg Gln Glu Ala Gly Tyr Thr Val Thr
                85                  90                  95 gat ctg cag tat cag tca tac tcg gtg att ccg gga aag cct gct ttg   336
Asp Leu Gln Tyr Gln Ser Tyr Ser Val Ile Pro Gly Lys Pro Ala Leu
            100                 105                 110 ccc ggt ctg cct tca acc ttt ggc agt gaa gag gat gtc aca act ttg   384
Pro Gly Leu Pro Ser Thr Phe Gly Ser Glu Glu Asp Val Thr Thr Leu
        115                 120                 125 gtg gtt cat ctg tac gac aac tac agc tcc atc gct gtg gat ctg tcg   432
Val Val His Leu Tyr Asp Asn Tyr Ser Ser Ile Ala Val Asp Leu Ser
    130                 135                 140 tac tca atc ttc cct aaa tat gac gcc att gtg cgc agc gcg aac gtt   480
Tyr Ser Ile Phe Pro Lys Tyr Asp Ala Ile Val Arg Ser Ala Asn Val
145                 150                 155                 160
```

-continued

| | |
|---|---|
| acg aac aag ggt act caa aat atc aca gtt gag gca ctg tcc agc ttc<br>Thr Asn Lys Gly Thr Gln Asn Ile Thr Val Glu Ala Leu Ser Ser Phe<br>               165                     170                    175 | 528 |
| agc ttc gat ttc cca tac gaa gat ctt gaa atg att agc ctc agg ggc<br>Ser Phe Asp Phe Pro Tyr Glu Asp Leu Glu Met Ile Ser Leu Arg Gly<br>           180                     185                    190 | 576 |
| gac tgg gcg aga gaa gcc cac cgt cag agg cga aag gtg gaa tac gga<br>Asp Trp Ala Arg Glu Ala His Arg Gln Arg Arg Lys Val Glu Tyr Gly<br>         195                     200                    205 | 624 |
| ctc caa ggc ttc gga agt agc act ggt ttc tcc tct cac ctg cac aac<br>Leu Gln Gly Phe Gly Ser Ser Thr Gly Phe Ser Ser His Leu His Asn<br>       210                   215                   220 | 672 |
| ccc ttt ctt gcg ata gtg cat ccc tcc act acg gaa tct cag ggt gag<br>Pro Phe Leu Ala Ile Val His Pro Ser Thr Thr Glu Ser Gln Gly Glu<br>225                     230                    235                240 | 720 |
| gcc tgg gga ttt aac ctt gtc tac aca ggc tcg ttc tcc gtt gat gtc<br>Ala Trp Gly Phe Asn Leu Val Tyr Thr Gly Ser Phe Ser Val Asp Val<br>                   245                    250                    255 | 768 |
| gag aag ggc tcc cag ggc ctc act cgc gct ctg ctg gga ttc aat ccc<br>Glu Lys Gly Ser Gln Gly Leu Thr Arg Ala Leu Leu Gly Phe Asn Pro<br>         260                     265                    270 | 816 |
| agt cag ctg tct tgg cag ctg ggt gcg ggc gag aca ctt acc tcg ccg<br>Ser Gln Leu Ser Trp Gln Leu Gly Ala Gly Glu Thr Leu Thr Ser Pro<br>       275                   280                   285 | 864 |
| gaa tgt gtt tca gtc tac tca agt gac ggc atc ggc ggc atg tct cgt<br>Glu Cys Val Ser Val Tyr Ser Ser Asp Gly Ile Gly Gly Met Ser Arg<br>         290                     295                    300 | 912 |
| tca ttc cat cgc ctc tac cgc aac cac ctg atc aag agc aag ttc gcc<br>Ser Phe His Arg Leu Tyr Arg Asn His Leu Ile Lys Ser Lys Phe Ala<br>305                     310                    315                320 | 960 |
| aca tcg gat cgc ccg ccg ctg ctg aac agc tgg gag ggt ctg tat ttc<br>Thr Ser Asp Arg Pro Pro Leu Leu Asn Ser Trp Glu Gly Leu Tyr Phe<br>                   325                    330                    335 | 1008 |
| gac tac aat gag agc aca atc tac cgc ttg gct gag gag tcg gcc gcc<br>Asp Tyr Asn Glu Ser Thr Ile Tyr Arg Leu Ala Glu Glu Ser Ala Ala<br>         340                     345                    350 | 1056 |
| ttg gga gtg aaa ctg ttc gtt atg gac gac ggt tgg ttc ggc gac aag<br>Leu Gly Val Lys Leu Phe Val Met Asp Asp Gly Trp Phe Gly Asp Lys<br>       355                   360                   365 | 1104 |
| tac ccc cgt gta tcg gat aac gcc ggt ctg ggt gac tgg gtg cct aac<br>Tyr Pro Arg Val Ser Asp Asn Ala Gly Leu Gly Asp Trp Val Pro Asn<br>370                     375                    380 | 1152 |
| ccg gac cgc ttt cct gat ggc cta acc ccc ctg gtg gaa gat gtc acg<br>Pro Asp Arg Phe Pro Asp Gly Leu Thr Pro Leu Val Glu Asp Val Thr<br>385                     390                    395                400 | 1200 |
| aag ctg aag gca gga aac tcc tca acc gac ctc cgc ttt ggc ctc tgg<br>Lys Leu Lys Ala Gly Asn Ser Ser Thr Asp Leu Arg Phe Gly Leu Trp<br>                   405                    410                    415 | 1248 |
| gtt gaa cca gaa atg gcc aac ccc aac tcg acc ctg tac cat gag cac<br>Val Glu Pro Glu Met Ala Asn Pro Asn Ser Thr Leu Tyr His Glu His<br>         420                     425                    430 | 1296 |
| cct gac tgg gtg ctt cat gcc ggc caa tac cca cgc acc ttg caa cgc<br>Pro Asp Trp Val Leu His Ala Gly Gln Tyr Pro Arg Thr Leu Gln Arg<br>       435                   440                   445 | 1344 |
| aac cag ctc gtg ctc aac ctt gct ttg cct gag gtg cag gac tat atc<br>Asn Gln Leu Val Leu Asn Leu Ala Leu Pro Glu Val Gln Asp Tyr Ile<br>       450                   455                   460 | 1392 |
| atc gat gag att acc aac atc ctc aac agc tcg gct att tcc tat gtg<br>Ile Asp Glu Ile Thr Asn Ile Leu Asn Ser Ser Ala Ile Ser Tyr Val<br>465                     470                    475                480 | 1440 |

```
              aag tgg gac ttc aac cgg gcg atg cac gag aca ccc tcc ccc agc aac     1488
              Lys Trp Asp Phe Asn Arg Ala Met His Glu Thr Pro Ser Pro Ser Asn
                                      485                 490                 495 gac cac gaa tac atc ctg ggc atg tac cgg gtg ttc gac acc ctg acc     1536
              Asp His Glu Tyr Ile Leu Gly Met Tyr Arg Val Phe Asp Thr Leu Thr
                              500                 505                 510 acg cgc ttc ccc gat gtt ctg tgg gaa ggt tgt gcc tct ggt ggt gga     1584
              Thr Arg Phe Pro Asp Val Leu Trp Glu Gly Cys Ala Ser Gly Gly Gly
                          515                 520                 525 cgt ttc gac ccc ggt gta ctt gag tac ttc ccg cag atc tgg acc tcc     1632
              Arg Phe Asp Pro Gly Val Leu Glu Tyr Phe Pro Gln Ile Trp Thr Ser
                      530                 535                 540 gac aac acc gat gcc ctg atg cgc atc acc atc cag cta ggt act tca     1680
              Asp Asn Thr Asp Ala Leu Met Arg Ile Thr Ile Gln Leu Gly Thr Ser
              545                 550                 555                 560 ctg gca tac cct ccg agc gcc atg ggt gcc cat ctc tca gca gtc ccg     1728
              Leu Ala Tyr Pro Pro Ser Ala Met Gly Ala His Leu Ser Ala Val Pro
                                  565                 570                 575 aat gcc cag act gga cgt acc att cct gtc aaa ttc cgt ggc cac gtc     1776
              Asn Ala Gln Thr Gly Arg Thr Ile Pro Val Lys Phe Arg Gly His Val
                              580                 585                 590 gcc atg atg ggc gga tca ttc ggt ctc gaa cta gac ccc gcc gag ctg     1824
              Ala Met Met Gly Gly Ser Phe Gly Leu Glu Leu Asp Pro Ala Glu Leu
                          595                 600                 605 cag gag gat gag aag gcc gaa gtc ccg gga ctg att gcc ctt gca gaa     1872
              Gln Glu Asp Glu Lys Ala Glu Val Pro Gly Leu Ile Ala Leu Ala Glu
                      610                 615                 620 aag gtt aac ccg atc atc ctg act ggc gat atg tgg cgt ctc agg ctt     1920
              Lys Val Asn Pro Ile Ile Leu Thr Gly Asp Met Trp Arg Leu Arg Leu
              625                 630                 635                 640 ccc gag gag tct aac tgg ccg gcg gtg cta ttc atc tct gag gat ggt     1968
              Pro Glu Glu Ser Asn Trp Pro Ala Val Leu Phe Ile Ser Glu Asp Gly
                                  645                 650                 655 aac caa gct gtc ctc ttc tac ttc cag ctc ggc cct aat gtt aac cat     2016
              Asn Gln Ala Val Leu Phe Tyr Phe Gln Leu Gly Pro Asn Val Asn His
                              660                 665                 670 gcc act ccc tgg ctc agg ctg cag gga ttg gat cct aag gcc acg tat     2064
              Ala Thr Pro Trp Leu Arg Leu Gln Gly Leu Asp Pro Lys Ala Thr Tyr
                          675                 680                 685 agc gtt gat gga aac gga tcg tac tct ggt gcg aca ttg atg aac atg     2112
              Ser Val Asp Gly Asn Gly Ser Tyr Ser Gly Ala Thr Leu Met Asn Met
                      690                 695                 700 gga ctg cag tac aag ttt gaa tcg gat tat gat agc aag gtg gtg ttc     2160
              Gly Leu Gln Tyr Lys Phe Glu Ser Asp Tyr Asp Ser Lys Val Val Phe
              705                 710                 715                 720 ttg cag aag cag                                                     2172
              Leu Gln Lys Gln <210> SEQ ID NO 9
<211> LENGTH: 724
<212> TYPE: PRT
<213> ORGANISM: Aspergillus oryzae

<400> SEQUENCE: 9

Gln Glu Thr Ser Ser Asn Asn Ala Val Val Ala Asp Gly Lys Thr Phe
1               5                   10                  15

Ala Leu Asn Gly Glu Asn Val Ser Tyr Arg Phe Arg Val Asn Glu Thr
            20                  25                  30

Thr Gly Asp Leu Val Ser Asp His Phe Gly Gly Ser Ile Thr Gly Asn
        35                  40                  45
```

-continued

```
Leu Phe Pro Gly Phe Gly Ala Glu Ala Leu Gly Gly Trp Val Gly Leu
 50                  55                  60
Ala Gly Arg Phe Arg Arg Glu Phe Pro Asp His Gly Arg Gly Asp Phe
 65                  70                  75                  80
Arg Ile Pro Ala Val Arg Ile Arg Gln Glu Ala Gly Tyr Thr Val Thr
                     85                  90                  95
Asp Leu Gln Tyr Gln Ser Tyr Ser Val Ile Pro Gly Lys Pro Ala Leu
                    100                 105                 110
Pro Gly Leu Pro Ser Thr Phe Gly Ser Glu Glu Asp Val Thr Thr Leu
                115                 120                 125
Val Val His Leu Tyr Asp Asn Tyr Ser Ser Ile Ala Val Asp Leu Ser
130                 135                 140
Tyr Ser Ile Phe Pro Lys Tyr Asp Ala Ile Val Arg Ser Ala Asn Val
145                 150                 155                 160
Thr Asn Lys Gly Thr Gln Asn Ile Thr Val Glu Ala Leu Ser Ser Phe
                    165                 170                 175
Ser Phe Asp Phe Pro Tyr Glu Asp Leu Glu Met Ile Ser Leu Arg Gly
                180                 185                 190
Asp Trp Ala Arg Glu Ala His Arg Gln Arg Arg Lys Val Glu Tyr Gly
            195                 200                 205
Leu Gln Gly Phe Gly Ser Ser Thr Gly Phe Ser Ser His Leu His Asn
210                 215                 220
Pro Phe Leu Ala Ile Val His Pro Ser Thr Thr Glu Ser Gln Gly Glu
225                 230                 235                 240
Ala Trp Gly Phe Asn Leu Val Tyr Thr Gly Ser Phe Ser Val Asp Val
                    245                 250                 255
Glu Lys Gly Ser Gln Gly Leu Thr Arg Ala Leu Leu Gly Phe Asn Pro
                260                 265                 270
Ser Gln Leu Ser Trp Gln Leu Gly Ala Gly Glu Thr Leu Thr Ser Pro
            275                 280                 285
Glu Cys Val Ser Val Tyr Ser Ser Asp Gly Ile Gly Gly Met Ser Arg
290                 295                 300
Ser Phe His Arg Leu Tyr Arg Asn His Leu Ile Lys Ser Lys Phe Ala
305                 310                 315                 320
Thr Ser Asp Arg Pro Pro Leu Leu Asn Ser Trp Glu Gly Leu Tyr Phe
                    325                 330                 335
Asp Tyr Asn Glu Ser Thr Ile Tyr Arg Leu Ala Glu Glu Ser Ala Ala
                340                 345                 350
Leu Gly Val Lys Leu Phe Val Met Asp Asp Gly Trp Phe Gly Asp Lys
            355                 360                 365
Tyr Pro Arg Val Ser Asp Asn Ala Gly Leu Gly Asp Trp Val Pro Asn
370                 375                 380
Pro Asp Arg Phe Pro Asp Gly Leu Thr Pro Leu Val Glu Asp Val Thr
385                 390                 395                 400
Lys Leu Lys Ala Gly Asn Ser Ser Thr Asp Leu Arg Phe Gly Leu Trp
                    405                 410                 415
Val Glu Pro Glu Met Ala Asn Pro Asn Ser Thr Leu Tyr His Glu His
                420                 425                 430
Pro Asp Trp Val Leu His Ala Gly Gln Tyr Pro Arg Thr Leu Gln Arg
            435                 440                 445
Asn Gln Leu Val Leu Asn Leu Ala Leu Pro Glu Val Gln Asp Tyr Ile
450                 455                 460
```

```
Ile Asp Glu Ile Thr Asn Ile Leu Asn Ser Ser Ala Ile Ser Tyr Val
465                 470                 475                 480

Lys Trp Asp Phe Asn Arg Ala Met His Glu Thr Pro Ser Pro Ser Asn
            485                 490                 495

Asp His Glu Tyr Ile Leu Gly Met Tyr Arg Val Phe Asp Thr Leu Thr
        500                 505                 510

Thr Arg Phe Pro Asp Val Leu Trp Glu Gly Cys Ala Ser Gly Gly Gly
    515                 520                 525

Arg Phe Asp Pro Gly Val Leu Glu Tyr Phe Pro Gln Ile Trp Thr Ser
530                 535                 540

Asp Asn Thr Asp Ala Leu Met Arg Ile Thr Ile Gln Leu Gly Thr Ser
545                 550                 555                 560

Leu Ala Tyr Pro Pro Ser Ala Met Gly Ala His Leu Ser Ala Val Pro
            565                 570                 575

Asn Ala Gln Thr Gly Arg Thr Ile Pro Val Lys Phe Arg Gly His Val
        580                 585                 590

Ala Met Met Gly Gly Ser Phe Gly Leu Glu Leu Asp Pro Ala Glu Leu
    595                 600                 605

Gln Glu Asp Glu Lys Ala Glu Val Pro Gly Leu Ile Ala Leu Ala Glu
610                 615                 620

Lys Val Asn Pro Ile Ile Leu Thr Gly Asp Met Trp Arg Leu Arg Leu
625                 630                 635                 640

Pro Glu Glu Ser Asn Trp Pro Ala Val Leu Phe Ile Ser Glu Asp Gly
            645                 650                 655

Asn Gln Ala Val Leu Phe Tyr Phe Gln Leu Gly Pro Asn Val Asn His
        660                 665                 670

Ala Thr Pro Trp Leu Arg Leu Gln Gly Leu Asp Pro Lys Ala Thr Tyr
    675                 680                 685

Ser Val Asp Gly Asn Gly Ser Tyr Ser Gly Ala Thr Leu Met Asn Met
690                 695                 700

Gly Leu Gln Tyr Lys Phe Glu Ser Asp Tyr Asp Ser Lys Val Val Phe
705                 710                 715                 720

Leu Gln Lys Gln

<210> SEQ ID NO 10
<211> LENGTH: 1014
<212> TYPE: DNA
<213> ORGANISM: Saccharomyces cerevisiae
<220> FEATURE:
<221> NAME/KEY: CDS
<222> LOCATION: (1)..(1014)
<223> OTHER INFORMATION: SED1 anchor

<400> SEQUENCE: 10 aaa tta tca act gtc cta tta tct gcc ggt tta gcc tcg act act ttg      48
Lys Leu Ser Thr Val Leu Leu Ser Ala Gly Leu Ala Ser Thr Thr Leu
1               5                   10                  15 gcc caa ttt tcc aac agt aca tct gct tct tcc acc gat gtc act tcc      96
Ala Gln Phe Ser Asn Ser Thr Ser Ala Ser Ser Thr Asp Val Thr Ser
            20                  25                  30 tcc tct tcc atc tcc act tcc tct ggc tca gta act atc aca tct tct     144
Ser Ser Ser Ile Ser Thr Ser Ser Gly Ser Val Thr Ile Thr Ser Ser
        35                  40                  45 gaa gct cca gaa tcc gac aac ggt acc agc aca gct gca cca act gaa     192
Glu Ala Pro Glu Ser Asp Asn Gly Thr Ser Thr Ala Ala Pro Thr Glu
50                  55                  60
```

| | | | | | | | | | | | | | | | | |
|---|---|---|---|---|---|---|---|---|---|---|---|---|---|---|---|---|
| acc | tca | aca | gag | gct | cca | acc | act | gct | atc | cca | act | aac | ggt | acc | tct | 240 |
| Thr | Ser | Thr | Glu | Ala | Pro | Thr | Thr | Ala | Ile | Pro | Thr | Asn | Gly | Thr | Ser | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| act | gaa | gct | cca | acc | act | gct | atc | cca | act | aac | ggt | acc | tct | act | gaa | 288 |
| Thr | Glu | Ala | Pro | Thr | Thr | Ala | Ile | Pro | Thr | Asn | Gly | Thr | Ser | Thr | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| gct | cca | act | gat | act | act | act | gaa | gct | cca | acc | acc | gct | ctt | cca | act | 336 |
| Ala | Pro | Thr | Asp | Thr | Thr | Thr | Glu | Ala | Pro | Thr | Thr | Ala | Leu | Pro | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| aac | ggt | act | tct | act | gaa | gct | cca | act | gat | act | act | act | gaa | gct | cca | 384 |
| Asn | Gly | Thr | Ser | Thr | Glu | Ala | Pro | Thr | Asp | Thr | Thr | Thr | Glu | Ala | Pro | |
| | | 115 | | | | | 120 | | | | | 125 | | | | |

| | | | | | | | | | | | | | | | | |
|---|---|---|---|---|---|---|---|---|---|---|---|---|---|---|---|---|
| acc | acc | ggt | ctt | cca | acc | aac | ggt | acc | act | tca | gct | ttc | cca | cca | act | 432 |
| Thr | Thr | Gly | Leu | Pro | Thr | Asn | Gly | Thr | Thr | Ser | Ala | Phe | Pro | Pro | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| aca | tct | ttg | cca | cca | agc | aac | act | acc | acc | act | cct | cct | tac | aac | cca | 480 |
| Thr | Ser | Leu | Pro | Pro | Ser | Asn | Thr | Thr | Thr | Thr | Pro | Pro | Tyr | Asn | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tct | act | gac | tac | acc | act | gac | tac | act | gta | gtc | act | gaa | tat | act | act | 528 |
| Ser | Thr | Asp | Tyr | Thr | Thr | Asp | Tyr | Thr | Val | Val | Thr | Glu | Tyr | Thr | Thr | |
| | | | 165 | | | | | 170 | | | | | 175 | | | |

| | | | | | | | | | | | | | | | | |
|---|---|---|---|---|---|---|---|---|---|---|---|---|---|---|---|---|
| tac | tgt | cca | gaa | cca | acc | act | ttc | acc | aca | aac | ggt | aag | act | tac | acc | 576 |
| Tyr | Cys | Pro | Glu | Pro | Thr | Thr | Phe | Thr | Thr | Asn | Gly | Lys | Thr | Tyr | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| gtc | act | gaa | cca | acc | aca | ttg | act | atc | act | gac | tgt | cca | tgc | acc | att | 624 |
| Val | Thr | Glu | Pro | Thr | Thr | Leu | Thr | Ile | Thr | Asp | Cys | Pro | Cys | Thr | Ile | |
| | | 195 | | | | | 200 | | | | | 205 | | | | |

| | | | | | | | | | | | | | | | | |
|---|---|---|---|---|---|---|---|---|---|---|---|---|---|---|---|---|
| gaa | aag | cca | aca | acc | aca | tca | acc | acc | gaa | tac | act | gta | gtc | act | gag | 672 |
| Glu | Lys | Pro | Thr | Thr | Thr | Ser | Thr | Thr | Glu | Tyr | Thr | Val | Val | Thr | Glu | |
| | 210 | | | | | 215 | | | | | 220 | | | | | |

| | | | | | | | | | | | | | | | | |
|---|---|---|---|---|---|---|---|---|---|---|---|---|---|---|---|---|
| tac | act | act | tac | tgt | cca | gaa | cca | acc | act | ttc | acc | aca | aac | ggt | aag | 720 |
| Tyr | Thr | Thr | Tyr | Cys | Pro | Glu | Pro | Thr | Thr | Phe | Thr | Thr | Asn | Gly | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| act | tac | acc | gtc | act | gaa | cca | acc | act | ttg | act | atc | act | gac | tgt | cca | 768 |
| Thr | Tyr | Thr | Val | Thr | Glu | Pro | Thr | Thr | Leu | Thr | Ile | Thr | Asp | Cys | Pro | |
| | | | 245 | | | | | 250 | | | | | 255 | | | |

| | | | | | | | | | | | | | | | | |
|---|---|---|---|---|---|---|---|---|---|---|---|---|---|---|---|---|
| tgt | act | att | gaa | aag | agc | gaa | gcc | cct | gag | tct | tct | gtc | cca | gtt | acc | 816 |
| Cys | Thr | Ile | Glu | Lys | Ser | Glu | Ala | Pro | Glu | Ser | Ser | Val | Pro | Val | Thr | |
| | | | | 260 | | | | | 265 | | | | | 270 | | |

| | | | | | | | | | | | | | | | | |
|---|---|---|---|---|---|---|---|---|---|---|---|---|---|---|---|---|
| gaa | tct | aag | ggc | act | acc | acc | aaa | gaa | aca | ggt | gtt | act | acc | aaa | caa | 864 |
| Glu | Ser | Lys | Gly | Thr | Thr | Thr | Lys | Glu | Thr | Gly | Val | Thr | Thr | Lys | Gln | |
| | | 275 | | | | | 280 | | | | | 285 | | | | |

| | | | | | | | | | | | | | | | | |
|---|---|---|---|---|---|---|---|---|---|---|---|---|---|---|---|---|
| acc | aca | gcc | aac | cca | agt | cta | acc | gtc | tcc | aca | gtc | gtc | cca | gtt | tca | 912 |
| Thr | Thr | Ala | Asn | Pro | Ser | Leu | Thr | Val | Ser | Thr | Val | Val | Pro | Val | Ser | |
| | 290 | | | | | 295 | | | | | 300 | | | | | |

| | | | | | | | | | | | | | | | | |
|---|---|---|---|---|---|---|---|---|---|---|---|---|---|---|---|---|
| tcc | tct | gct | tct | tct | cat | tcc | gtt | gtc | atc | aac | agt | aac | ggt | gct | aac | 960 |
| Ser | Ser | Ala | Ser | Ser | His | Ser | Val | Val | Ile | Asn | Ser | Asn | Gly | Ala | Asn | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| gtc | gtc | gtt | cca | ggt | gct | tta | ggt | ttg | gct | ggt | gtt | gct | atg | tta | ttc | 1008 |
| Val | Val | Val | Pro | Gly | Ala | Leu | Gly | Leu | Ala | Gly | Val | Ala | Met | Leu | Phe | |
| | | | | 325 | | | | | 330 | | | | | 335 | | |

| | | | |
|---|---|---|---|
| tta | taa | | 1014 |
| Leu | | | |

<210> SEQ ID NO 11
<211> LENGTH: 337
<212> TYPE: PRT
<213> ORGANISM: Saccharomyces cerevisiae

<400> SEQUENCE: 11

```
Lys Leu Ser Thr Val Leu Leu Ser Ala Gly Leu Ala Ser Thr Thr Leu
1               5                   10                  15
Ala Gln Phe Ser Asn Ser Thr Ser Ala Ser Ser Thr Asp Val Thr Ser
            20                  25                  30
Ser Ser Ser Ile Ser Thr Ser Ser Gly Ser Val Thr Ile Thr Ser Ser
        35                  40                  45
Glu Ala Pro Glu Ser Asp Asn Gly Thr Ser Thr Ala Ala Pro Thr Glu
    50                  55                  60
Thr Ser Thr Glu Ala Pro Thr Thr Ala Ile Pro Thr Asn Gly Thr Ser
65                  70                  75                  80
Thr Glu Ala Pro Thr Thr Ala Ile Pro Thr Asn Gly Thr Ser Thr Glu
                85                  90                  95
Ala Pro Thr Asp Thr Thr Thr Glu Ala Pro Thr Thr Ala Leu Pro Thr
            100                 105                 110
Asn Gly Thr Ser Thr Glu Ala Pro Thr Asp Thr Thr Glu Ala Pro
        115                 120                 125
Thr Thr Gly Leu Pro Thr Asn Gly Thr Thr Ser Ala Phe Pro Pro Thr
    130                 135                 140
Thr Ser Leu Pro Pro Ser Asn Thr Thr Thr Thr Pro Pro Tyr Asn Pro
145                 150                 155                 160
Ser Thr Asp Tyr Thr Thr Asp Tyr Thr Val Val Thr Glu Tyr Thr Thr
                165                 170                 175
Tyr Cys Pro Glu Pro Thr Thr Phe Thr Thr Asn Gly Lys Thr Tyr Thr
            180                 185                 190
Val Thr Glu Pro Thr Thr Leu Thr Ile Thr Asp Cys Pro Cys Thr Ile
        195                 200                 205
Glu Lys Pro Thr Thr Thr Ser Thr Thr Glu Tyr Thr Val Val Thr Glu
    210                 215                 220
Tyr Thr Thr Tyr Cys Pro Glu Pro Thr Thr Phe Thr Thr Asn Gly Lys
225                 230                 235                 240
Thr Tyr Thr Val Thr Glu Pro Thr Thr Leu Thr Ile Thr Asp Cys Pro
                245                 250                 255
Cys Thr Ile Glu Lys Ser Glu Ala Pro Glu Ser Ser Val Pro Val Thr
            260                 265                 270
Glu Ser Lys Gly Thr Thr Lys Glu Thr Gly Val Thr Thr Lys Gln
        275                 280                 285
Thr Thr Ala Asn Pro Ser Leu Thr Val Ser Thr Val Val Pro Val Ser
    290                 295                 300
Ser Ser Ala Ser Ser His Ser Val Val Ile Asn Ser Asn Gly Ala Asn
305                 310                 315                 320
Val Val Val Pro Gly Ala Leu Gly Leu Ala Gly Val Ala Met Leu Phe
                325                 330                 335
Leu
```

<210> SEQ ID NO 12
<211> LENGTH: 591
<212> TYPE: DNA
<213> ORGANISM: Saccharomyces cerevisiae
<220> FEATURE:
<221> NAME/KEY: misc_feature
<222> LOCATION: (1)..(591)
<223> OTHER INFORMATION: SAG1 terminator

```
<400> SEQUENCE: 12
aacgggtact gtacagttag tacattgagt cgaaatatac gaaattattg ttcataattt      60
tcatcctggc tcttttttc ttcaaccata gttaaatgga cagttcatat cttaactcta     120
ataatacttt tctagttctt atccttttcc gtctcaccgc agattttatc atagtattaa    180
atttatattt tgttcgtaaa aagaaaaatt tgtgagcgtt accgctcgtt tcattacccg    240
aaggctgttt cagtagacca ctgattaagt aagtagatga aaaaatttca tcaccatgaa    300
agagttcgat gagagctact ttttcaaatg cttaacagct aaccgccatt caataatgtt    360
acgctctctt cattctgcgg ctacgttatc taacaagagg ttttactctc tcatatctca    420
ttcaaataga aagaacataa tcaaatctag agtcgacttg gttgaacacg ttgccaaggc    480
ttaagtgaat ttactttaaa tcttgcattt aaataaattt tcttttata gcttatgac     540 ttagtttcaa tttatatact attttaatga cattttcgat tcattgattg a             591

<210> SEQ ID NO 13
<211> LENGTH: 2181
<212> TYPE: DNA
<213> ORGANISM: Artificial Sequence
<220> FEATURE:
<223> OTHER INFORMATION: AOAglC for Lac
<220> FEATURE:
<221> NAME/KEY: CDS
<222> LOCATION: (1)..(2181)

<400> SEQUENCE: 13 atg gca caa gaa acc tct agt aat aat gca gtg gtg gca gat ggc aag        48
Met Ala Gln Glu Thr Ser Ser Asn Asn Ala Val Val Ala Asp Gly Lys
1               5                   10                  15 acc ttt gct ttg aat ggt gaa aac gtg tca tac cgc ttt cgt gtt aat        96
Thr Phe Ala Leu Asn Gly Glu Asn Val Ser Tyr Arg Phe Arg Val Asn
            20                  25                  30 gaa act acg ggt gat tta gtt agt gat cat ttt ggt ggt tca att acg       144
Glu Thr Thr Gly Asp Leu Val Ser Asp His Phe Gly Gly Ser Ile Thr
        35                  40                  45 ggt aat ttg ttt cca ggt ttt ggt gct gaa gca tta ggt ggt tgg gtt       192
Gly Asn Leu Phe Pro Gly Phe Gly Ala Glu Ala Leu Gly Gly Trp Val
    50                  55                  60 ggt tta gct ggt cgg ttt cgt cgg gaa ttt cca gat cat ggt cgt ggt       240
Gly Leu Ala Gly Arg Phe Arg Arg Glu Phe Pro Asp His Gly Arg Gly
65                  70                  75                  80 gat ttt cgg att cca gct gtt cgt att cgg caa gaa gca ggt tat act       288
Asp Phe Arg Ile Pro Ala Val Arg Ile Arg Gln Glu Ala Gly Tyr Thr
                85                  90                  95 gtt acg gat tta caa tac caa agt tac tca gtt att cca ggt aaa cca       336
Val Thr Asp Leu Gln Tyr Gln Ser Tyr Ser Val Ile Pro Gly Lys Pro
            100                 105                 110 gct tta cca ggt tta cca agt act ttt ggt tca gaa gaa gat gtt act       384
Ala Leu Pro Gly Leu Pro Ser Thr Phe Gly Ser Glu Glu Asp Val Thr
        115                 120                 125 acg tta gtt gtt cat ttg tac gat aac tat agt tca att gca gtt gat       432
Thr Leu Val Val His Leu Tyr Asp Asn Tyr Ser Ser Ile Ala Val Asp
    130                 135                 140 tta agt tat tca att ttt cca aaa tat gat gct att gtt cgt agt gca       480
Leu Ser Tyr Ser Ile Phe Pro Lys Tyr Asp Ala Ile Val Arg Ser Ala
145                 150                 155                 160 aac gtt act aac aag ggt acg caa aac att act gtt gaa gca tta agt       528
Asn Val Thr Asn Lys Gly Thr Gln Asn Ile Thr Val Glu Ala Leu Ser
                165                 170                 175
```

-continued

| | |
|---|---|
| agt ttt agt ttt gat ttt cca tat gaa gat tta gaa atg att tca tta<br>Ser Phe Ser Phe Asp Phe Pro Tyr Glu Asp Leu Glu Met Ile Ser Leu<br>               180                       185                 190 | 576 |
| cgg ggt gat tgg gct cgt gaa gca cat cgg caa cgt cgg aaa gtt gaa<br>Arg Gly Asp Trp Ala Arg Glu Ala His Arg Gln Arg Arg Lys Val Glu<br>        195                    200                    205 | 624 |
| tat ggt tta caa ggt ttt ggt agt tca acg ggt ttt agt tca cat tta<br>Tyr Gly Leu Gln Gly Phe Gly Ser Ser Thr Gly Phe Ser Ser His Leu<br>210                       215                    220 | 672 |
| cat aac cca ttt tta gct att gtt cat cca agt act acg gaa tca caa<br>His Asn Pro Phe Leu Ala Ile Val His Pro Ser Thr Thr Glu Ser Gln<br>225                          230                    235                    240 | 720 |
| ggt gaa gca tgg ggt ttt aac ttg gtt tac act ggt agt ttt tca gtt<br>Gly Glu Ala Trp Gly Phe Asn Leu Val Tyr Thr Gly Ser Phe Ser Val<br>               245                       250                    255 | 768 |
| gat gtt gaa aag ggt agt caa ggt tta acg cgt gca ttg ttg ggt ttt<br>Asp Val Glu Lys Gly Ser Gln Gly Leu Thr Arg Ala Leu Leu Gly Phe<br>        260                    265                    270 | 816 |
| aac cca agt caa ttg tca tgg caa tta ggt gct ggt gaa act tta acg<br>Asn Pro Ser Gln Leu Ser Trp Gln Leu Gly Ala Gly Glu Thr Leu Thr<br>275                       280                    285 | 864 |
| agt cca gaa tgt gtt tca gtt tat agt tca gat ggt att ggt ggt atg<br>Ser Pro Glu Cys Val Ser Val Tyr Ser Ser Asp Gly Ile Gly Gly Met<br>        290                    295                    300 | 912 |
| agt cgt tca ttt cat cgt ttg tac cgg aac cat ttg att aag agt aag<br>Ser Arg Ser Phe His Arg Leu Tyr Arg Asn His Leu Ile Lys Ser Lys<br>305                       310                    315                    320 | 960 |
| ttt gct acg tca gat cgg cca cca tta tta aat agt tgg gaa ggt tta<br>Phe Ala Thr Ser Asp Arg Pro Pro Leu Leu Asn Ser Trp Glu Gly Leu<br>               325                       330                    335 | 1008 |
| tac ttt gat tac aac gaa agt act att tac cgt ttg gca gaa gaa tca<br>Tyr Phe Asp Tyr Asn Glu Ser Thr Ile Tyr Arg Leu Ala Glu Glu Ser<br>        340                    345                    350 | 1056 |
| gct gca tta ggt gtt aag tta ttt gtt atg gat gat ggt tgg ttt ggt<br>Ala Ala Leu Gly Val Lys Leu Phe Val Met Asp Asp Gly Trp Phe Gly<br>355                          360                    365 | 1104 |
| gat aag tat cca cgt gtt tca gat aat gct ggt tta ggc gat tgg gtt<br>Asp Lys Tyr Pro Arg Val Ser Asp Asn Ala Gly Leu Gly Asp Trp Val<br>370                       375                    380 | 1152 |
| cca aat cca gat cgg ttt cca gat ggt tta acg cca tta gtt gaa gat<br>Pro Asn Pro Asp Arg Phe Pro Asp Gly Leu Thr Pro Leu Val Glu Asp<br>385                          390                    395                    400 | 1200 |
| gtt act aag tta aag gca ggt aat agt tca act gat tta cgg ttt ggt<br>Val Thr Lys Leu Lys Ala Gly Asn Ser Ser Thr Asp Leu Arg Phe Gly<br>               405                       410                    415 | 1248 |
| tta tgg gtt gaa cca gaa atg gca aac cca aac agt acg ttg tac cat<br>Leu Trp Val Glu Pro Glu Met Ala Asn Pro Asn Ser Thr Leu Tyr His<br>        420                    425                    430 | 1296 |
| gaa cat cca gat tgg gtt tta cac gct ggt caa tat cca cgt act tta<br>Glu His Pro Asp Trp Val Leu His Ala Gly Gln Tyr Pro Arg Thr Leu<br>435                          440                    445 | 1344 |
| caa cgg aat caa tta gtt tta aat tta gca tta cca gaa gtt caa gat<br>Gln Arg Asn Gln Leu Val Leu Asn Leu Ala Leu Pro Glu Val Gln Asp<br>450                          455                    460 | 1392 |
| tac att att gat gaa att acg aac att tta aat agt tca gct att agt<br>Tyr Ile Ile Asp Glu Ile Thr Asn Ile Leu Asn Ser Ser Ala Ile Ser<br>465                       470                    475                    480 | 1440 |
| tac gtt aag tgg gat ttt aat cgt gca atg cat gaa acg cca agt cca<br>Tyr Val Lys Trp Asp Phe Asn Arg Ala Met His Glu Thr Pro Ser Pro<br>               485                       490                    495 | 1488 |

| | | |
|---|---|---|
| tca aac gat cat gaa tac att ttg ggc atg tac cgt gtt ttt gat act<br>Ser Asn Asp His Glu Tyr Ile Leu Gly Met Tyr Arg Val Phe Asp Thr<br>                  500                        505                  510 | | 1536 |
| ttg act acg cgg ttt cca gat gtt tta tgg gaa ggt tgt gct agt ggt<br>Leu Thr Thr Arg Phe Pro Asp Val Leu Trp Glu Gly Cys Ala Ser Gly<br>                  515                        520                  525 | | 1584 |
| ggt ggt cgt ttt gat cca ggt gtt tta gaa tac ttt cca caa att tgg<br>Gly Gly Arg Phe Asp Pro Gly Val Leu Glu Tyr Phe Pro Gln Ile Trp<br>                  530                        535                  540 | | 1632 |
| acg tca gat aat act gat gct tta atg cgg att acg att caa tta ggt<br>Thr Ser Asp Asn Thr Asp Ala Leu Met Arg Ile Thr Ile Gln Leu Gly<br>545                        550                        555                  560 | | 1680 |
| act agt tta gca tat cca cca tca gct atg ggt gca cat tta agt gct<br>Thr Ser Leu Ala Tyr Pro Pro Ser Ala Met Gly Ala His Leu Ser Ala<br>                  565                        570                  575 | | 1728 |
| gtt cca aat gca caa act ggt cgt acg att cca gtt aaa ttt cgg ggt<br>Val Pro Asn Ala Gln Thr Gly Arg Thr Ile Pro Val Lys Phe Arg Gly<br>                  580                        585                  590 | | 1776 |
| cat gtt gct atg atg ggt ggt tca ttt ggt tta gaa tta gat cca gct<br>His Val Ala Met Met Gly Gly Ser Phe Gly Leu Glu Leu Asp Pro Ala<br>                595                        600                  605 | | 1824 |
| gaa tta caa gaa gat gaa aaa gca gaa gtt cca ggt tta att gct ttg<br>Glu Leu Gln Glu Asp Glu Lys Ala Glu Val Pro Gly Leu Ile Ala Leu<br>610                        615                        620 | | 1872 |
| gca gaa aag gtt aac cca att att tta act ggt gat atg tgg cgt tta<br>Ala Glu Lys Val Asn Pro Ile Ile Leu Thr Gly Asp Met Trp Arg Leu<br>625                        630                        635                  640 | | 1920 |
| cgg tta cca gaa gaa agt aac tgg cca gct gtt ttg ttt att tca gaa<br>Arg Leu Pro Glu Glu Ser Asn Trp Pro Ala Val Leu Phe Ile Ser Glu<br>                  645                        650                  655 | | 1968 |
| gat ggt aac caa gca gtt ttg ttt tat ttt caa ttg ggt cca aac gtt<br>Asp Gly Asn Gln Ala Val Leu Phe Tyr Phe Gln Leu Gly Pro Asn Val<br>                  660                        665                  670 | | 2016 |
| aac cat gct acg cca tgg tta cgg tta caa ggt tta gat cca aag gca<br>Asn His Ala Thr Pro Trp Leu Arg Leu Gln Gly Leu Asp Pro Lys Ala<br>                675                        680                  685 | | 2064 |
| act tat agt gtt gat ggt aat ggt agt tat tca ggt gct acg tta atg<br>Thr Tyr Ser Val Asp Gly Asn Gly Ser Tyr Ser Gly Ala Thr Leu Met<br>690                        695                        700 | | 2112 |
| aat atg ggt tta caa tac aag ttt gaa agt gat tat gat tct aag gtc<br>Asn Met Gly Leu Gln Tyr Lys Phe Glu Ser Asp Tyr Asp Ser Lys Val<br>705                        710                        715                  720 | | 2160 |
| gtg ttt tta caa aag caa tag<br>Val Phe Leu Gln Lys Gln<br>                      725 | | 2181 |

<210> SEQ ID NO 14
<211> LENGTH: 726
<212> TYPE: PRT
<213> ORGANISM: Artificial Sequence
<220> FEATURE:
<223> OTHER INFORMATION: Synthetic Construct

<400> SEQUENCE: 14

Met Ala Gln Glu Thr Ser Ser Asn Asn Ala Val Val Ala Asp Gly Lys
1                  5                        10                        15

Thr Phe Ala Leu Asn Gly Glu Asn Val Ser Tyr Arg Phe Arg Val Asn
                  20                        25                        30

Glu Thr Thr Gly Asp Leu Val Ser Asp His Phe Gly Gly Ser Ile Thr
        35                        40                        45

Gly Asn Leu Phe Pro Gly Phe Gly Ala Glu Ala Leu Gly Gly Trp Val
 50                  55                  60

Gly Leu Ala Gly Arg Phe Arg Arg Glu Phe Pro Asp His Gly Arg Gly
 65                  70                  75                  80

Asp Phe Arg Ile Pro Ala Val Arg Ile Arg Gln Glu Ala Gly Tyr Thr
                 85                  90                  95

Val Thr Asp Leu Gln Tyr Gln Ser Tyr Ser Val Ile Pro Gly Lys Pro
            100                 105                 110

Ala Leu Pro Gly Leu Pro Ser Thr Phe Gly Ser Glu Glu Asp Val Thr
        115                 120                 125

Thr Leu Val Val His Leu Tyr Asp Asn Tyr Ser Ser Ile Ala Val Asp
    130                 135                 140

Leu Ser Tyr Ser Ile Phe Pro Lys Tyr Asp Ala Ile Val Arg Ser Ala
145                 150                 155                 160

Asn Val Thr Asn Lys Gly Thr Gln Asn Ile Thr Val Glu Ala Leu Ser
                165                 170                 175

Ser Phe Ser Phe Asp Phe Pro Tyr Glu Asp Leu Glu Met Ile Ser Leu
            180                 185                 190

Arg Gly Asp Trp Ala Arg Glu Ala His Arg Gln Arg Arg Lys Val Glu
        195                 200                 205

Tyr Gly Leu Gln Gly Phe Gly Ser Ser Thr Gly Phe Ser Ser His Leu
    210                 215                 220

His Asn Pro Phe Leu Ala Ile Val His Pro Ser Thr Thr Glu Ser Gln
225                 230                 235                 240

Gly Glu Ala Trp Gly Phe Asn Leu Val Tyr Thr Gly Ser Phe Ser Val
                245                 250                 255

Asp Val Glu Lys Gly Ser Gln Gly Leu Thr Arg Ala Leu Leu Gly Phe
            260                 265                 270

Asn Pro Ser Gln Leu Ser Trp Gln Leu Gly Ala Gly Glu Thr Leu Thr
        275                 280                 285

Ser Pro Glu Cys Val Ser Val Tyr Ser Ser Asp Gly Ile Gly Gly Met
    290                 295                 300

Ser Arg Ser Phe His Arg Leu Tyr Arg Asn His Leu Ile Lys Ser Lys
305                 310                 315                 320

Phe Ala Thr Ser Asp Arg Pro Leu Leu Asn Ser Trp Glu Gly Leu
                325                 330                 335

Tyr Phe Asp Tyr Asn Glu Ser Thr Ile Tyr Arg Leu Ala Glu Glu Ser
            340                 345                 350

Ala Ala Leu Gly Val Lys Leu Phe Val Met Asp Asp Gly Trp Phe Gly
        355                 360                 365

Asp Lys Tyr Pro Arg Val Ser Asp Asn Ala Gly Leu Gly Asp Trp Val
    370                 375                 380

Pro Asn Pro Asp Arg Phe Pro Asp Gly Leu Thr Pro Leu Val Glu Asp
385                 390                 395                 400

Val Thr Lys Leu Lys Ala Gly Asn Ser Ser Thr Asp Leu Arg Phe Gly
                405                 410                 415

Leu Trp Val Glu Pro Glu Met Ala Asn Pro Asn Ser Thr Leu Tyr His
            420                 425                 430

Glu His Pro Asp Trp Val Leu His Ala Gly Gln Tyr Pro Arg Thr Leu
        435                 440                 445

Gln Arg Asn Gln Leu Val Leu Asn Leu Ala Leu Pro Glu Val Gln Asp
        450                 455                 460

Tyr Ile Ile Asp Glu Ile Thr Asn Ile Leu Asn Ser Ser Ala Ile Ser
465                 470                 475                 480

Tyr Val Lys Trp Asp Phe Asn Arg Ala Met His Glu Thr Pro Ser Pro
                485                 490                 495

Ser Asn Asp His Glu Tyr Ile Leu Gly Met Tyr Arg Val Phe Asp Thr
            500                 505                 510

Leu Thr Thr Arg Phe Pro Asp Val Leu Trp Glu Gly Cys Ala Ser Gly
        515                 520                 525

Gly Gly Arg Phe Asp Pro Gly Val Leu Glu Tyr Phe Pro Gln Ile Trp
    530                 535                 540

Thr Ser Asp Asn Thr Asp Ala Leu Met Arg Ile Thr Ile Gln Leu Gly
545                 550                 555                 560

Thr Ser Leu Ala Tyr Pro Pro Ser Ala Met Gly Ala His Leu Ser Ala
                565                 570                 575

Val Pro Asn Ala Gln Thr Gly Arg Thr Ile Pro Val Lys Phe Arg Gly
            580                 585                 590

His Val Ala Met Met Gly Gly Ser Phe Gly Leu Glu Leu Asp Pro Ala
        595                 600                 605

Glu Leu Gln Glu Asp Glu Lys Ala Glu Val Pro Gly Leu Ile Ala Leu
    610                 615                 620

Ala Glu Lys Val Asn Pro Ile Ile Leu Thr Gly Asp Met Trp Arg Leu
625                 630                 635                 640

Arg Leu Pro Glu Glu Ser Asn Trp Pro Ala Val Leu Phe Ile Ser Glu
                645                 650                 655

Asp Gly Asn Gln Ala Val Leu Phe Tyr Phe Gln Leu Gly Pro Asn Val
            660                 665                 670

Asn His Ala Thr Pro Trp Leu Arg Leu Gln Gly Leu Asp Pro Lys Ala
        675                 680                 685

Thr Tyr Ser Val Asp Gly Asn Gly Ser Tyr Ser Gly Ala Thr Leu Met
    690                 695                 700

Asn Met Gly Leu Gln Tyr Lys Phe Glu Ser Asp Tyr Asp Ser Lys Val
705                 710                 715                 720

Val Phe Leu Gln Lys Gln
                725

<210> SEQ ID NO 15
<211> LENGTH: 25
<212> TYPE: DNA
<213> ORGANISM: Artificial Sequence
<220> FEATURE:
<223> OTHER INFORMATION: pgsA-Cter-Fw

<400> SEQUENCE: 15
aatttcgctt ggaaagtaga agacg                                    25

<210> SEQ ID NO 16
<211> LENGTH: 25
<212> TYPE: DNA
<213> ORGANISM: Artificial Sequence
<220> FEATURE:
<223> OTHER INFORMATION: AOAglC-for lac-Cter-Rv

<400> SEQUENCE: 16
ccatcaacac tataagttgc ctttg                                    25

MICROORGANISM CAPABLE OF DISPLAYING α-GALACTOSIDASE ON SURFACE LAYER THEREOF, AND USE THEREOF

TECHNICAL FIELD

The present invention relates to a microorganism capable of displaying α-galactosidase on its surface layer, and use thereof.

BACKGROUND ART

Soybean molasses produced during industrial soybean processing is often treated as waste. Soybean molasses contains oligosaccharides such as raffinose and stachyose. However, raffinose and stachyose are oligosaccharides containing an α-1,6 linked galactose residue. As an enzyme that hydrolyzes this bond, α-galactosidase is known (Non-Patent Document 1). However, many microorganisms cannot degrade these oligosaccharides.

Therefore, there has been demand to develop a means for utilizing, as a sugar raw material, soybean molasses that is discarded in such a manner.

Incidentally, yeast capable of displaying proteins such as enzymes on its cell surface has been produced. Examples of proteins to be displayed on such surface-display yeast include lipases, amylases (e.g., glucoamylase and α-amylase), and cellulases (e.g., endoglucanase, cellobiohydrolase, and β-glucosidase). This surface-display yeast is used to produce biodiesel or bioethanol (Patent Documents 1 to 4 and Non-Patent Document 2).

RELATED ART DOCUMENTS

Patent Documents

Patent Document 1: JP H11-290078A
Patent Document 2: WO 02/085935
Patent Document 3: WO 2015/033948
Patent Document 4: WO 2016/017736

Non-Patent Documents

Non-Patent Document 1: Eur. J. Biochem., 268, 2982-2990 (2001)
Non-Patent Document 2: Biotechnology for Biofuels, 7(1):8 (2014)
Non-Patent Document 3: Seibutsu-kogaku (Journal of the Society for Biotechnology, Japan), Vol. 89, No. 4, 154-160 (2011) and its partial translation
Non-Patent Document 4: Proceedings of the Society of Chemical Engineers, Japan, 70$^{th}$ Annual Meeting, Session ID F123
Non-Patent Document 5: Appl. Environ. Microbiol., 72(1), 269-275 (2006)
Non-Patent Document 6: Appl. Environ. Microbiol., 74(4), 1117-1123 (2008)
Non-Patent Document 7: Appl. Microbiol. Biotechnol., 81, 711-719 (2008)
Non-Patent Document 8: Appl. Microbiol. Biotechnol., 84:733-739 (2009)
Non-Patent Document 9: Reports of the Graduate School/Faculty of Engineering, Tottori University, Vol. 47, 12-27 (2016)

SUMMARY OF THE INVENTION

Problem to be Solved by the Invention

It is an object of the present invention to provide a microorganism capable of degrading oligosaccharides such as raffinose and stachyose via an α-1,6 linkage, which may occur in soybean molasses.

Means for Solving the Problem

The present invention provides a transformed microorganism capable of displaying α-galactosidase on its surface layer.

In an embodiment, the α-galactosidase is α-galactosidase C (AglC).

In an embodiment, the microorganism has an alcohol fermentation ability.

In an embodiment, the microorganism is a yeast.

In an embodiment, the yeast belongs to the genus *Saccharomyces, Pichia, Schizosaccharomyces, Kluyveromyces,* or *Candida.*

In an embodiment, the yeast is *Saccharomyces cerevisiae.*

In an embodiment, the microorganism is a lactic bacterium.

In an embodiment, the transformed microorganism is an inactivated microorganism.

The present invention provides an enzyme agent comprising the transformed microorganism.

The present invention provides a method for producing alcohol, comprising:
a step of culturing the transformed microorganism having an alcohol fermentation ability in a culture medium containing a material that contains an oligosaccharide containing α-1,6 linked α-galactose.

In an embodiment, the alcohol is ethanol.

The present invention provides a method for saccharifying a material that contains an oligosaccharide containing α-1,6 linked α-galactose, the method comprising:
a step of combining the transformed microorganism and/or the enzyme agent with the material that contains the oligosaccharide containing α-1,6 linked α-galactose.

The present invention provides a method for producing lactic acid, comprising:
a step of obtaining a saccharified material by combining the transformed microorganism and/or the enzyme agent with a material that contains an oligosaccharide containing α-1,6 linked α-galactose, and
a step of culturing a lactic acid bacterium in a culture medium containing the saccharified material.

The present invention provides a method for producing lactic acid, comprising:
a step of culturing the transformed microorganism being a lactic acid bacterium in a culture medium containing a material that contains an oligosaccharide containing α-1,6 linked α-galactose.

In an embodiment, the oligosaccharide containing α-1,6 linked α-galactose includes at least one sugar of raffinose, stachyose, melibiose, and verbascose.

Effects of the Invention

According to the present invention, it is provided that a surface-display microorganism capable of hydrolyzing oligosaccharides containing α-1,6 linked α-galactose, which may occur in soybean molasses. This makes it possible to utilize soybean molasses as a sugar raw material for the microorganism.

Figure 1:
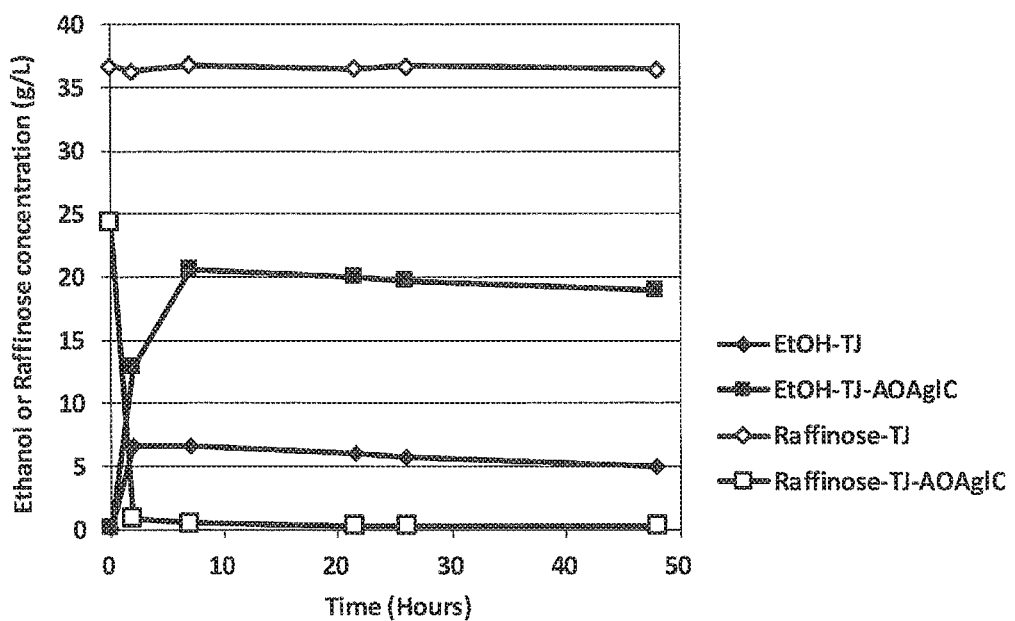
FIG. 1 is a graph showing the ethanol fermentation generated from culturing yeast capable of displaying α-galactosidase on its surface layer in a liquid culture medium containing raffinose.

DESCRIPTION OF EMBODIMENTS (Microorganism Capable of Displaying α-Galactosidase on its Surface Layer)

α-Galactosidase has a function of cleaving an α-1,6 linkage between the constituent saccharides of a galactose-containing oligosaccharide, examples of which include raffinose and stachyose (Non-Patent Document 1). α-Galactosidase also cleaves an α-1,6 linkage between p-nitrophenyl and D-galactose in p-nitrophenyl α-D-galactopyranoside.

There is no particular limitation on α-galactosidase to be displayed as long as it is an enzyme that has a function of cleaving an α-1,6 linkage as mentioned above. For example, α-galactosidase is classified into four types, namely types A to D, and all of these types may be used. The C-type ("AglC") is preferable. For example, α-Galactosidase may be derived from microorganisms belonging to the genera *Aspergillus*, *Penicillium*, *Trichoderma*, and *Phanerochaete*, and examples of such microorganisms include *Aspergillus oryzae*, *Aspergillus niger*, *Aspergillus terreus*, *Aspergillus tamarii*, *Penicillium simplicissimum*, *Trichoderma reesei*, and *Phanerochaete chrysosporium* (Non-Patent Document 1).

The sequences of α-galactosidase and the gene encoding α-galactosidase can be obtained using a method that is commonly used by a person skilled in the art, based on the sequence information registered in institutions such as GenBank and NITE (DOGAN). For example, the registration number of α-galactosidase C derived from *Aspergillus oryzae* (also referred to as "AOAglC") is XM_001827585, and its base sequence and its amino acid sequence are as shown in SEQ ID Nos. 1 and 2), respectively.

The gene encoding α-galactosidase (e.g., AOAglC) may be obtained as a nucleic acid fragment by performing PCR using, as a template, any nucleic acid derived from DNAs extracted from a microorganism (e.g., *Aspergillus oryzae*) from which it is derived, various cDNA libraries or genomic libraries, with a primer pair (e.g., SEQ ID Nos. 3 and 4) designed based on its base sequence (e.g., base sequence of SEQ ID No. 1), for example. The gene encoding α-galactosidase (e.g., AOAglc) may be obtained as any nucleic acid derived from the above-mentioned libraries by using a probe designed based on its base sequence (e.g., base sequence of SEQ ID No. 1). The gene coding for α-galactosidase (e.g., AOAglC) may also be synthesized as a nucleic acid fragment using any method for synthesizing a nucleic acid sequence known in the art, such as a chemical synthesis method.

Here, the gene or polynucleotide to be used herein may encode a protein that has an amino acid sequence obtained by deletion, substitution, or addition of one or several amino acids in the disclosed amino acid sequence and that substantially has a desired function or effect in the present invention. Any one of or a combination of two or more of the amino acid mutations (e.g., deletion, substitution, or addition) may be introduced into the disclosed amino acid sequence. The total number of mutations is not particularly limited. Examples of the total number of mutations include one or more and ten or less, or one or more and five or less. With respect to examples of amino acid substitution, any substitution may be used as long as a function or effect is substantially retained Conservative substitution may be used, for example. Examples of the conservative substitution include substitution within the following groups (i.e., between the amino acids in parentheses): (glycine, alanine), (valine, isoleucine, leucine), (aspartic acid, glutamic acid), (asparagine, glutamine), (serine, threonine), (lysine, arginine), and (phenylalanine, tyrosine).

In another embodiment, the gene or polynucleotide may encode a protein that has an amino acid sequence having 70% or more sequence identity to the disclosed amino acid sequence, and substantially has a desired function or effect in the present invention. Moreover, the sequence identity of the amino acid sequence can be 74% or more, 78% or more, 80% or more, 85% or more, 90% or more, 92% or more, 95% or more, 98% or more, or 99% or more.

Sequence identity or similarity as used herein refers to, as is known in the art, the relationship between two or more proteins or two or more polynucleotides that is determined by comparing the sequences. The "identity" of sequences means the degree of sequence invariance between protein sequences or polynucleotide sequences as determined by an alignment between the protein sequences or polynucleotide sequences or in some cases by an alignment between a series of partial sequences. The "similarity" means the degree of correlation between protein sequences or polynucleotide sequences as determined by an alignment between the protein sequences or polynucleotide sequences or in some cases by an alignment between a series of partial sequences. More specifically, the similarity is determined based on the sequence identity and conservativeness (substitution that maintains a particular amino acid in a sequence or physicochemical properties of a sequence). It should be noted that the similarity is called "Similarity" in sequence homology search results of BLAST, which will be described later. It is preferable that the method for determining the identity and similarity is a method that is designed so that the alignment between sequences to be compared becomes the longest. Methods for determining the identity and similarity are offered as programs available to the public. For example, the BLAST (Basic Local Alignment Search Tool) program by Altschul et al. (e.g., Altschul et al., J. Mol. Biol., 1990, 215: 403-410; Altschyl et al., Nucleic Acids Res., 1997, 25: 3389-3402) can be used for determination. Although there is no particular limitation on the conditions in the case where software such as BLAST is used, it is preferable to use default values.

In yet another embodiment, the gene or polynucleotide may be that hybridizing with a DNA having a base sequence complementary to a DNA having the disclosed base sequence in stringent conditions. The stringent conditions refer to conditions in which a so-called specific hybrid is formed while nonspecific hybrid is not formed, for example. An example thereof is conditions in which a complementary strand of a nucleic acid whose base sequence has high identity, DNA that has a base sequence having 70% or more, 75% or more, 78% or more, 80% or more, 85% or more, 90% or more, 92% or more, 95% or more, 98% or more, or 99% or more identity to the disclosed base sequence, for example, hybridizes, while a complementary strand of a nucleic acid having homology lower than that does not hybridize. More specifically, such conditions include a sodium salt concentration of 15 mM to 750 mM, 50 mM to 750 mM, or 300 mM to 750 mM, for example, a temperature of 25° C. to 70° C., 50° C. to 70° C., or 55° C. to 65° C., for example, and a formamide concentration of 0% to 50%, 20% to 50%, or 35% to 45%, for example. Furthermore, in the stringent conditions, washing conditions for a filter after the hybridization include a sodium salt concentration of 15 mM to 600 mM, 50 mM to 600 mM, or 300 mM to 600 mM, for example, and a temperature of 50° C. to 70° C., 55° C. to 70° C., or 60° C. to 65° C., for example. An example of a DNA that hybridizes in stringent conditions is a DNA that can be obtained by performing hybridization at 65° C. in the presence of 0.7 to 1.0 M NaCl using a filter on which a DNA is immobilized and then washing the filter in an SSC solution having 0.1 to 2 times concentration (SSC solution of one time concentration has a composition containing 150 mM NaCl and 15 mM sodium citrate) at 65° C. Hybridization can be performed using a well-known method such as a method described in Sambrook et al., Molecular Cloning, A Laboratory Manual, 3rd Ed., Cold Spring Harbor Laboratory (2001), for example. The higher the temperature is or the lower the salt concentration is, the higher the stringency is, thus making it possible to isolate a polynucleotide having higher homology (sequence identity).

In yet another embodiment, examples of the gene or polynucleotide include those that have a base sequence having 65% or more, 70% or more, 75% or more, 78% or more, 80% or more, 85% or more, 90% or more, 92% or more, 95% or more, 98% or more, or 99% or more identity to the disclosed base sequence, and substantially have a desired function or effect.

Substitution based on degeneracy of a genetic code can also be performed on a base sequence encoding a predetermined amino acid sequence to substitute at least one base in the base sequence encoding the predetermined amino acid sequence with a different base without changing the amino acid sequence of a protein. In yet another embodiment, the gene or polynucleotide to be used in the present invention also encompasses a DNA having a base sequence changed by substitution based on degeneracy of a genetic code. The gene encoding α-galactosidase may be artificially synthesized while codon optimization is performed, depending on the host microorganism.

A transformed microorganism capable of displaying α-galactosidase on its surface layer (also referred to simply as "microorganism capable of displaying α-galactosidase on its surface layer", "surface-display microorganism", or "transformed microorganism") is produced by transforming a host microorganism using a surface-display cassette (which will be described below) including the α-galactosidase gene.

There is no particular limitation on the host microorganism, and examples thereof include yeast, lactic acid bacteria, filamentous fungi, corynebacteria, *Escherichia coli*, and *Zymomonas* bacteria. Microorganisms that have an alcohol (e.g., ethanol) fermentation ability are preferable from the viewpoint of application to alcohol production, and examples of such microorganisms include yeast and *Zymomonas* bacteria. Lactic acid bacteria are preferable from the viewpoint of application to lactic acid production.

Examples of the types of yeast include those belonging to the genera *Saccharomyces, Pichia, Schizosaccharomyces, Kluyveromyces*, and *Candida*. Yeast belonging to the genus *Saccharomyces* are preferable, and *Saccharomyces cerevisiae* is more preferable. Examples of the strains of *Saccharomyces cerevisiae* include *Saccharomyces cerevisiae* NBRC1440 strain (available from National Institute of Technology and Evaluation), *Saccharomyces cerevisiae* TJ14 strain (Moukamnerd et al, Appl. Microbiol. Biotechnol., 2010, Vol. 88, p. 87-94), and *Saccharomyces cerevisiae* KF-7 strain (Ting et al., Process Biochem., 2006, Vol. 41, p. 909-914). In addition, examples of the strains of yeast include *Pichia pastoris* GS115 (manufactured by Invitrogen), *Pichia anomala* NBRC10213 strain, *Schizosaccharomyces pombe* NBRC1628 strain, *Kluyveromyces lactis* NBRC1267 strain, *Kluyveromyces marxianus* NBRC1777 strain (Yanase et al., Appl Microbiol Biotechnol, 2010, Vol. 88, p. 381-388), and *Candida utilis* NBRC0988 strain (Tomita et al., PLoS One. 2012; 7(5); e37226) (All NBRC strains are available from National Institute of Technology and Evaluation).

The term "lactic acid bacterium" is a general term for bacteria that produce lactic acid from sugars through metabolism or fermentation. The lactic acid bacterium may be mainly classified into four types, namely *Bifidobacterium, Enterococcus, Lactobacillus*, and *Streptococcus*. Lactobacilli may be preferably used. Examples of the lactic acid bacterium include bacteria belonging to the genus *Streptococcus, Lactobacillus, Bifidobacterium, Lactococcus, Pediococcus*, or *Leuconostoc*. Examples of the lactic acid bacterium include *Streptococcus thermophilus, Streptococcus cremoris, Streptococcus faecalis, Streptococcus lactis, Lactobacillus bulgaricus, Lactobacillus acidophilus, Lactobacillus casei, Lactobacillus delbrueckii, Lactobacillus arabinosus, Lactobacillus caucasicus, Lactobacillus lactis, Lactobacillus Leishmanni, Lactobacillus musicus, Lactobacillus thermophilus, Lactobacillus plantarum, Bifidobacterium bifidum, Bifidobacterium adolescentis, Bifidobacte-

*rium longum, Bifidobacterium breve, Bifidobacterium infantis, Lactococcus lactis, Lactococcus cremoris, Pediococcus damnosus*, and *Leuconostoc mesenteroides*. The lactic acid bacterium also includes spore-forming lactic acid bacteria. The term "spore-forming lactic acid bacterium" is a general term for lactic acid bacteria that form spores. Examples of the spore-forming lactic acid bacterium include bacteria belonging to the genus *Bacillus*. The spore-forming lactic acid bacterium belonging to the genus *Bacillus* may have thermal resistance (they can grow at a high temperature such as 45° C., for example), a high-speed fermentation ability, and an ability to utilize a wide variety of sugars. Examples of the bacterium belonging to the genus *Bacillus* include *Bacillus coagulans* (also known as "sporolactobacillus") and *Bacillus lincheniformis*.

The lactic acid bacterium may be genetically engineered. Examples thereof include recombinant microorganisms into which either of the L- or D-lactic acid synthase gene is introduced, and recombinant microorganisms in which either of the L- or D-lactic acid synthase gene is disrupted. Examples of such recombinant microorganisms include the *Lactobacillus plantarum* ldhL1::amyA strain (Okano et al., Appl. Environ. Microbiol. 2009, Vol. 75, 462-467) and the *Lactobacillus plantarum* ΔldhL1::PxylAB-xpk1::tkt-Δxpk2::PxylAB strain (Yoshida et al., Appl. Microbiol. Biotechnol., 2011, Vol. 92, 67-76). The *Lactobacillus plantarum* ldhL1::amyA strain is a recombinant strain that secretes α-amylase and produces D-lactic acid from glucose, and the *Lactobacillus plantarum* ΔldhL1::PxylAB-xpk1::tkt-Δxpk2::PxylAB strain is a recombinant strain that produces D-lactic acid from both glucose and xylose.

For example, galactose and/or sucrose may be produced by hydrolyzing raffinose, stachyose, melibiose, or verbascose. It is preferable that the microorganism capable of displaying α-galactosidase on its surface layer can perform alcohol fermentation or lactic fermentation using at least one of sucrose and galactose. In one embodiment, the microorganism capable of displaying α-galactosidase on its surface layer may use glucose and at least one of sucrose and galactose to perform fermentation. The microorganism capable of displaying α-galactosidase on its surface layer may be further genetically engineered so that it can utilize galactose, for example.

As described in detail below, a surface-display cassette for displaying α-galactosidase on the surface layer can be produced. The surface-display cassette includes the gene encoding α-galactosidase as well as DNAs encoding a secretion signal and an anchor domain. The surface-display cassette may be arranged between a promoter and a terminator. A cell surface-localized protein or a cell membrane binding region thereof may be used as the anchor domain. The "cell surface-localized protein" refers to a protein that is immobilized on or attaches or adheres to a cell surface layer and is localized on the cell surface layer. Lipid-modified proteins are known as the cell surface-localized protein and are immobilized on a cell membrane through a covalent bond between the lipid and membrane components. For example, as the surface display techniques for various host microorganisms, the techniques disclosed in Patent Documents 1 to 4 and Non-Patent Document 2 (yeast), Non-Patent Documents 3 to 6 (lactic acid bacteria), Non-Patent Document 7 (filamentous fungi), Non-Patent Document 8 (corynebacteria), Non-Patent Document 4 (*Escherichia coli*), Non-Patent Document 9 (*Zymomonas* bacteria), and the like can be used.

Cell surface display techniques for yeast that are known to the person skilled in the art may be employed, and a GPI anchor (Patent Documents 1, 3, and 4, and Non-Patent Document 2) or sugar chain-binding domain (Patent Documents 2 and 3) of a cell surface-localized protein can be used.

A typical example of the cell surface-localized protein is a GPI (glycosyl phosphatidyl inositol: glycolipid having, as a basic structure, ethanolamine phosphate-6 mannose α-1,2 mannose α-1,6 mannose α-1,4 glucosamine α-1,6 inositol phospholipid) anchor protein. The GPI anchor protein has glycolipid GPI at its C-terminus, and is bound to the cell membrane surface through a covalent bond between the GPI and PI (phosphatidyl inositol) in the cell membrane.

Examples of the cell surface display technologies using the GPI anchor include a method using a surface-display cassette containing a recombinant DNA formed by: a DNA encoding a secretion signal peptide—a gene of interest—a DNA encoding a GPI anchor adhesion recognition signal. GPI is bound to the C-terminus of the GPI anchor protein as follows. After transcription and translation, the GPI anchor protein is secreted into the lumen of the endoplasmic reticulum due to an action of a secretion signal present on the N-terminal side. A region that is recognized when a GPI anchor is bound to a GPI anchor protein, called a GPI anchor attachment signal, is present at or near the C-terminus of the GPI anchor protein. In the lumen of the endoplasmic reticulum and the Golgi body, the GPI anchor attachment signal region is cleaved, and GPI is bound to a newly generated C-terminus.

The protein to which the GPI is bound is transferred through secretion vesicles to the cell membrane, and is immobilized on the cell membrane through a covalent bond of the GPI with the PI in the cell membrane. Then, the GPI anchor is cleaved by phosphatidylinositol-dependent phospholipase C (PI-PLC), and the protein is incorporated into the cell wall so as to be displayed on the cell surface in the state of being immobilized on the cell wall.

A polynucleotide that encodes the entirety of a GPI anchor protein, which is a cell surface-localized protein, or a region including a GPI anchor attachment signal region, which is a cell membrane binding region thereof can be used to provide a surface-display microorganism. The cell membrane binding region (GPI anchor attachment signal region) is generally a region on the C-terminal side of the cell surface-localized protein. It is sufficient that the cell membrane-binding region includes the GPI anchor attachment signal region, and the cell membrane-binding region may further include any other moiety of the GPI anchor protein as long as the enzyme activity of the fusion protein is not inhibited.

It is sufficient that the GPI anchor protein is a protein that functions in a yeast cell. Examples of such a GPI anchor protein include α-agglutinin or α-agglutinin (AGα1, AGA1), TIP1, FLO1, SED1, CWP1, and CWP2. For example, SED1 is a main cell surface-localized protein during the stationary phase of yeast *Saccharomyces cerevisiae*, and the gene thereof can be obtained using a method that is commonly used by a person skilled in the art, based on the sequence information registered in GenBank, for example (GenBank accession number NM_001180385; NCBI Gene ID:851649). For example, a GPI anchor adhesion recognition signal sequence that exists in the sequence of 320 amino acids from the C-terminus of yeast α-agglutinin may also be used as the anchor domain.

For example, in a polynucleotide including a coding sequence of a secretion signal, a structural gene encoding a cell surface-localized protein, and a coding sequence of a GPI anchor adhesion recognition signal, all or a portion of the structural gene can be replaced with the gene encoding α-galactosidase.

Examples of the cell surface display technique using the sugar chain-binding domain include a method using a surface-display cassette containing a recombinant DNA in which an enzyme is bound to the N-terminus, the C-terminus or both the N-terminus and the C-terminus of the cell-surface localized protein (flocculation functional domain). The enzyme that is expressed from this recombinant DNA and secreted out of the cell membrane may stay on the cell surface layer because a plurality of sugar chains in the sugar chain-binding domain interact with the sugar chains in the cell wall. Examples of the flocculation functional domain include a sugar chain-binding site of lectin, lectin-like protein or the like, and typically the flocculation functional domain of the GPI anchor protein.

As the anchor protein of the surface-display cassette, the following may also be used: for lactic acid bacteria, a CA domain of a peptide glycan binding protein AcmA, and a PgsA protein, which is a subunit of a poly-γ-glutamate synthetase complex (PgsBCA) derived from *Baccilus subtilis* (Non-Patent Documents 3 to 6); for filamentous fungi, a CWP anchor and an MP1 anchor (membrane binding protein) derived from *Aspergillus oryzae* (Non-Patent Document 7); for corynebacteria, porin (cell wall binding protein) derived from *Corynebacterium glutamicum* (Non-Patent Document 8); for *Escherichia coli*, the PgsA protein, which has been described in the above description regarding lactic acid bacteria (Non-Patent Document 4); and for *Zymomonas* bacteria, an anchoring region (INPN) that is present in the N-terminal region of the ice nucleating protein gene derived from *Pseudomonas syringae* (Non-Patent Document 9).

The secretion signal is not particularly limited, and may be a secretion signal of α-galactosidase to be displayed, a secretion signal sequence of the cell-surface localized protein, or another secretion signal capable of leading the enzyme out of the cell. A portion or all of the secretion signal sequence and pro-sequence may remain at the N-terminus after the cell surface display, as long as there is no influence on the enzyme activity.

In the present invention, any promoter and any terminator may be used. The promoter DNA used may be that originally contained in a gene to be expressed or that derived from another gene. A promoter and a terminator of a gene encoding a cell surface-localized protein to be used as the anchor domain may also be used. For example, when SED1 is used as the anchor domain, the promoter of the same SED1 may be used. For example, when SED1 is used as the anchor domain, the terminator of α-agglutinin, which is a different cell surface-localized protein, may also be used. The promoters and terminators of GAPDH (glyceraldehyde 3'-phosphate dehydrogenase), PGK (phosphoglycerate kinase), PYK (pyruvate kinase), and TPI (triosephosphate isomerase) can also be used as the promoter and the terminator.

The construction of the surface-display cassette or the synthesis and linkage of the recombinant DNA can be performed, for example, using a method that is commonly used by a person skilled in the art. A linker may be used as appropriate to link DNAs.

The surface-display cassette or recombinant DNA may be incorporated into an expression vector. The expression vector may include factors such as a selective marker and an enhancer as appropriate. The expression vector is in a plasmid form, for example. For example, a plasmid having the replication origin (Ori) of the yeast 2 μm plasmid and the replication origin of ColE1 is preferably used for yeast. It is preferable that the plasmid has a selective marker and a replication gene for *Escherichia coli* in that the plasmid preparation and the detection of a transformant are facilitated. Examples of the selective marker include a drug resistance gene and an auxotrophic gene. Examples of the drug resistance gene include, but are not particularly limited to, the ampicillin resistance gene (Ampr) and the kanamycin resistance gene (Kanr) Examples of the auxotrophic gene include, but are not particularly limited to, the N-(5'-phosphoribosyl)anthranilate isomerase (TRP1) gene, the tryptophan synthase (TRP5) gene, the β-isopropylmalate dehydrogenase (LEU2) gene, the imidazoleglycerol-phosphate dehydrogenase (HIS3) gene, the histidinol dehydrogenase (HIS4) gene, the dihydroorotate dehydrogenase (URA1) gene, and the orotidine-5-phosphate decarboxylase (URA3) gene. A replication gene for yeast may be selected as needed. Also, in the cases of other microorganisms, vectors, factors, and the like that are well known to a person skilled in the art may be used.

There is no particular limitation on a method for introducing the surface-display cassette or recombinant DNA to a host. Examples thereof include a lithium acetate method, an electroporation method, and a protoplast method.

Transformed microorganisms may be selected using the selective marker. For example, an antibody against the α-galactosidase can be used to confirm that α-galactosidase is displayed on the surface layer of the microorganism. Alternatively, confirmation can be made through activity evaluation using a synthetic substrate, p-nitrophenyl α-D-galactopyranoside.

The microorganism capable of displaying α-galactosidase on its surface layer itself may be inactivated (for example, the metabolic function or fermentation ability is eliminated). The microorganism capable of displaying α-galactosidase on its surface layer may be inactivated through heat treatment (e.g., a technique such as heating, cryopreservation, lyophilization, or low-temperature drying). Even when the surface-display microorganism is inactivated in this manner, for example, the displayed α-galactosidase may still remain active.

The inactivated surface-display microorganism may be used as an α-galactosidase enzyme agent. Examples of the enzyme agent include a suspension containing the microorganism capable of displaying α-galactosidase on its surface layer and a culture medium that can maintain the surface-display microorganism, and the heat-treated surface-display microorganism (for example, heat-treated using a technique such as heating, cryopreservation, lyophilization, or low-temperature drying). As described below, a form in which the surface-display microorganism is immobilized on a carrier is also possible.

The surface-display microorganism may be immobilized on a carrier. This enables reuse in a method described below.

A carrier and a method that are commonly used by a person skilled in the art are used as the carrier for immobilization and the immobilization method. Examples of the immobilization method include a carrier binding method, an entrapment method, and a cross-linking method.

A porous material is preferably used as the carrier. Preferable examples thereof include foams and resins such as polyvinyl alcohol, polyurethane foam, polystyrene foam, polyacrylamide, polyvinyl formal resin porous material, and silicone foam. The sizes of the openings of the porous material may be determined in consideration of the type and size of microorganism to be used, and are preferably in a range of 50 to 1000 μm in the case of practical yeast.

There is no limitation on the shape of the carrier. A spherical shape or pillar shape (e.g., cubic shape) is preferable in view of the strength of the carrier and culture efficiency. It is sufficient that the size thereof may be determined depending on the microorganism to be used, but in general, a spherical shape with a diameter of 2 to 50 mm when the carrier is or a 2- to 50-mm square pillar shape is preferable.

(Method for Producing Alcohol)

According to the present invention, it is provided a method for producing alcohol using the surface-display microorganism. The surface-display microorganism has an alcohol fermentation ability. The alcohol production method includes a step of culturing the surface-display microorganism having an alcohol fermentation ability in a culture medium containing a material that contains an oligosaccharide containing α-1,6 linked α-galactose.

The number of saccharides in the oligosaccharide containing α-1,6 linked α-galactose (also referred to as "α-galactose-containing oligosaccharide" hereinafter) is 2 to 5, preferably 2 to 4, and more preferably 3 to 4, for example. Examples of the oligosaccharide containing α-1,6 linked α-galactose include raffinose, stachyose, melibiose, and verbascose. Raffinose is an oligosaccharide (trisaccharide) in which glucose of sucrose is linked to galactose via an α-1,6 linkage. Stachyose is an oligosaccharide (tetrasaccharide) in which yet another galactose is linked to the galactose of raffinose via an α-1,6 linkage. Melibiose is an oligosaccharide (disaccharide) in which galactose is linked to glucose via an α-1,6 linkage. Verbascose is an oligosaccharide (pentasaccharide) in which yet another galactose is linked to the galactose of stachyose via an α-1,6 linkage. The "oligosaccharide containing α-1,6 linked α-galactose" includes raffinose, stachyose, melibiose, or verbascose, or a mixture of two or more of them, for example. In one embodiment, the α-galactose-containing oligosaccharide includes at least one sugar of raffinose, stachyose, melibiose, and verbascose.

In this specification, a step of culturing a microorganism to produce alcohol through the fermentation by the microorganism is also referred to as "alcohol fermentation step". A material used as a sugar raw material in the alcohol fermentation step is also referred to as "fermentation substrate". In one embodiment, the alcohol is ethanol.

The "fermentation substrate" in the alcohol fermentation step includes a material that contains the α-galactose-containing oligosaccharide, and may further include sugars (e.g., glucose, sucrose, and the like) other than the oligosaccharide.

The "material that contains an oligosaccharide containing α-1,6 linked α-galactose" (also referred to as "α-galactose-containing oligosaccharide-containing material" hereinafter) encompasses both an oligosaccharide alone and a mixture of an oligosaccharide and another component. The "α-galactose-containing oligosaccharide-containing material" contains at least one sugar of the sugars corresponding to the α-galactose-containing oligosaccharides (e.g., raffinose, stachyose, melibiose, and verbascose). A material that contains "at least one of raffinose, stachyose, melibiose, and verbascose" encompasses both a material that contains any one of raffinose, stachyose, melibiose, and verbascose, and a material that contains a combination of two or more of them. The oligosaccharides containing α-1,6 linked α-galactose, such as raffinose, stachyose, melibiose, and verbascose, are oligosaccharides contained in soybeans, and thus are also referred to as "soybean oligosaccharides". The "material that contains an oligosaccharide containing α-1,6 linked α-galactose" encompasses both a soybean-derived material and a non-soybean-derived material. The "material that contains an oligosaccharide containing α-1,6 linked α-galactose" may contain a sugar other than the α-galactose-containing oligosaccharides, and the sugar other than the oligosaccharides may be a monosaccharide or an oligosaccharide containing two or more saccharides. Examples thereof include sucrose and galactose. Soybean molasses may be preferably used as the soybean-derived material. The "soybean molasses" is soluble matter of soybeans, and may be collected from insoluble matter of soybeans through washing using alcohol or acid, for example. The "soybean molasses" may be waste produced during soybean processing, or may be obtained by concentrating soluble matter of soybeans produced during the soybean processing such that the resultant concentrate is rich in an oligosaccharide containing α-1,6 linked α-galactose (e.g., raffinose, stachyose, melibiose, or verbascose, or a mixture thereof).

In the alcohol production method of the present invention, the alcohol fermentation step may be performed under normal conditions in which fermentation is performed or microorganisms are cultured for the fermentation. A liquid culture is preferable. Such fermentation may be performed in an appropriate fermenter, for example.

The alcohol fermentation medium may also contain a component that is necessary or desirable for the growth of a microorganism to be used, in addition to the above-mentioned α-galactose-containing oligosaccharide-containing material. The reaction temperature during the alcohol fermentation step may be determined depending on a microorganism to be used, and it may be set to, for example, 30° C. to 37° C., and preferably 30° C. to 35° C. The fermentation pH is set to, for example, 4 to 8, and preferably 5 to 7. The fermentation culture may be performed anaerobically (the dissolved oxygen concentration may be for example 1 ppm or less, preferably about 0.3 ppm or less, and more preferably 0.1 ppm or less).

Examples of the form of the alcohol fermentation step include a batch process, a fed-batch process, a repeated batch process, and a continuous process, and its form may be any of them.

The microorganism input amount (the microorganism cell concentration at the start of fermentation), the initial feed amount of the fermentation substrate and the feed amount and feed timing of the additional fermentation substrate as required, and the fermentation time may be determined as appropriate depending on requirements such as the type and state of substrate, the volume of the fermentation culture, and the target amount of ethanol to be produced through fermentation. The yeast cell concentration at the start of fermentation is for example, 2 g (wet weight)/L to 50 g (wet weight)/L ($1 \times 10^7$ cells/mL to $2.5 \times 10^8$ cells/mL), and preferably 4 g (wet weight)/L to 20 g (wet weight)/L ($2 \times 10^7$ cells/mL to $1 \times 10^8$ cells/mL). The initial feed amount is, for example, 5 (w/v) % to 50 (w/v) %, and preferably 10 (w/v) % to 25 (w/v) %, with respect to the fermentation solution (total of the culture medium and yeast cells to be used for fermentation). The feed amount and feed timing of the additional fermentation substrate may be determined while the viscosity of the fermentation medium due to the progress of the fermentation, the amount of produced alcohol, generated carbon dioxide, or the like is monitored.

Since the alcohol fermentation conditions vary as the fermentation progresses, it is preferable to adjust the conditions to be within certain ranges. It is sufficient that changes over time in the fermentation are monitored using means as commonly used by a person skilled in the art, such as gas chromatography or HPLC.

After the fermentation step has finished, the culture medium containing alcohol (e.g., ethanol) is removed from the fermenter, and ethanol is isolated therefrom through an isolation process as commonly used by a person skilled in the art, examples thereof including separation using a centrifuge, and distillation. The surface-display microorganisms used for the fermentation can also be collected through solid-liquid separation (e.g., centrifugation or filtration), for example, and reused.

(Saccharification Method)

Combining the α-galactose-containing oligosaccharide-containing material with a transformed microorganism (surface-display microorganism) and/or an enzyme agent makes it possible to hydrolyze the α-galactose-containing oligosaccharide (e.g., raffinose, stachyose, melibiose, or verbascose) to produce sugars containing a smaller number of saccharides, such as sucrose (disaccharide) or galactose (monosaccharide) (this process is also referred to as "saccharification" in this specification). The present invention provides a method for saccharifying a soybean oligosaccharide-containing material, and this method includes a step of combining an α-galactose-containing oligosaccharide-containing material with a transformed microorganism and/or an enzyme agent. A "saccharified material" is obtained following this combining step. Herein, this combining step is also referred to as "saccharification step". The "saccharified material" may include at least one sugar of galactose, sucrose, fructose, and glucose, for example.

The combining conditions (e.g., a temperature, pH, and time) may be determined depending on the amount of the α-galactose-containing oligosaccharide-containing material to be used, the amount of the transformed microorganism or the enzyme agent, the characteristics of the surface-display microorganism, and the like. It is preferable to inactivate the transformed microorganism (for example, to eliminate the metabolic function or fermentation ability) in advance.

A saccharification product (including sucrose (disaccharide) or galactose (monosaccharide), for example) derived from the "α-galactose-containing oligosaccharide-containing material" may be used for subsequent fermentation (e.g., alcohol fermentation or lactic fermentation), for example. The saccharification product may be isolated or purified using a means well known to a person skilled in the art. The surface-display microorganisms used for the saccharification can also be collected through solid-liquid separation (e.g., centrifugation or filtration), for example, and reused.

(Method for Producing Lactic Acid)

The present invention provides a method for producing lactic acid, and this method includes the above-mentioned saccharification step and a step of culturing a lactic acid bacterium. With the present invention, lactic acid can be produced by culturing a lactic acid bacterium in a culture medium containing a product (saccharified material) produced through the saccharification step. Alternatively, the present invention provides another method for producing lactic acid, and this method includes a step of culturing a transformed lactic acid bacterium capable of displaying α-galactosidase on its surface layer (also referred to as "transformed lactic acid bacterium" or "surface-display lactic acid bacterium") in a culture medium containing an α-galactose-containing oligosaccharide-containing material.

Herein, a step of culturing a lactic acid bacterium or a transformed lactic acid bacterium (surface-display lactic acid bacterium) to produce lactic acid through the fermentation by the lactic acid bacterium or the transformed lactic acid bacterium is also referred to as "lactic fermentation step". A material used as a sugar raw material in the lactic fermentation step is also referred to as "lactic fermentation substrate". The "lactic fermentation substrate" includes a "saccharified material" or an "α-galactose-containing oligosaccharide-containing material", and may further include sugars derived from that other than these materials (e.g., sugars derived from the culture medium). The "lactic acid bacterium" is as described above.

In the lactic acid production method of the present invention, the lactic fermentation step may be performed under normal conditions in which fermentation is performed or a lactic acid bacterium is cultured for the fermentation. A liquid culture is preferable. Such fermentation may be performed in an appropriate fermenter, for example.

The lactic fermentation medium may also contain a component that is necessary or desirable for the growth of a microorganism to be used, in addition to the above-mentioned α-galactose-containing oligosaccharide-containing material or a saccharified product thereof.

There is no particular limitation on the lactic fermentation step, and a normal lactic fermentation method can be used. The pH for the lactic fermentation varies depending on the type of microorganism to be used, the type of culture medium, and the culture conditions, and may thus be determined appropriately as needed. The fermentation pH is set to, for example, 4 to 8, preferably 5 to 7, and more preferably 5.5 to 6.8. Since the pH may shift to the acidic side due to the produced lactic acid, it is preferable to regulate the pH throughout the period of the fermentation step. The fermentation culture may be performed anaerobically.

The culture of lactic acid bacterium or transformed lactic acid bacterium capable of displaying α-galactosidase on its surface layer may be through batch culture, semibatch culture, or continuous culture. Semibatch culture or continuous culture in which only saccharides are added during the culture may also be used. The culture time varies depending on the bacterial strain to be used, the components of a culture medium, and particularly the amount of saccharides, and in the case of batch culture, the culture time is for, for example, 0.5 days to 10 days, preferably 1 day to 7 days, and more preferably 1 day to 4 days. In the case of continuous culture or semibatch culture, the culture time is not limited thereto. Fermentation residue may be used as a bacterial bed. For example, after a single batch of fermentation has finished, the lactic acid producing microorganisms contained in the fermentation residue may be reused in a subsequent batch of fermentation.

The input amount of lactic acid bacterium or transformed lactic acid bacterium capable of displaying α-galactosidase on its surface layer ("lactic acid bacterium cell concentration at the start of fermentation"), the initial feed amount of the fermentation substrate and the feed amount and feed timing of the additional fermentation substrate as required, and the fermentation time may be determined as appropriate depending on requirements such as the type and state of substrate, the volume of the fermentation culture, and the target amount of lactic acid to be produced through fermentation. The lactic acid bacterium cell concentration at the start of fermentation is, for example, 0.01 g (wet weight)/L to 200 g (wet weight)/L ($2\times10^6$ cells/mL to $4\times10^{10}$ cells/mL), and preferably 5 g (wet weight)/L to 100 g (wet weight)/L ($1\times10^9$ cells/mL to $2\times10^{10}$ cells/mL). The initial feed amount is, for example, 1 (w/v) % to 99 (w/v) %, and preferably 5 (w/v) % to 90 (w/v) %, with respect to the fermentation solution (total of the culture medium and bacterial cells to be used for fermentation). The feed amount and feed timing of the additional fermentation substrate may be determined while the viscosity of the fermentation medium due to the progress of the fermentation, the amount of produced lactic acid or generated carbon dioxide, and the like are monitored.

The fermentation culture temperature may be set in consideration of the culture conditions such as the temperature at which the lactic acid producing microorganism to be used grow and the temperature at which an enzyme to be added functions. For example, the temperature may be set to 25° C. to 45° C., 30° C. to 40° C., or 35° C. to 37° C., but a higher or lower temperature may also be used particularly depending on the type of lactic acid producing microorganism to be used. In a case where the lactic acid producing microorganism to be used is a heat-resistant microorganism such as a spore-forming lactic acid bacterium, the temperature may be set to a higher temperature such as a temperature near 45° C.

Lactic acid in the form of lactic acid or an alkali salt of lactic acid may be collected by removing the bacterial cells from the culture solution after the culture. There is no particular limitation on a method of collecting lactic acid from the culture solution, and a known method may be used. An example thereof is a method disclosed in WO 2007/114017. Also, examples thereof include a method of allowing lactic acid to be adsorbed by an ion-exchange resin and then eluting lactic acid therefrom after washing the ion-exchange resin; a method of reacting lactic acid with alcohol (e.g., methanol or ethanol) in the presence of sulfuric acid to form an ester and then performing distillation; and a method of collecting and purifying lactic acid as a insoluble lactate such as magnesium lactate.

Also, the production of lactic acid encompasses the production of a product containing lactic acid. For example, after a lactic acid bacterium or transformed lactic acid bacterium has produced lactic acid, the fermentation solution may be collected as it is, or lactic acid may be collected together with the bacterial cells and/or the fermentation residue (e.g., sugars). For example, in a case where lactic acid is produced from soybean molasses, after a lactic acid bacterium or transformed lactic acid bacterium is cultured, a product (e.g., feed) containing produced lactic acid, lactic acid bacterial cells, and saccharified soybean molasses which is the residue of fermentation can be obtained as a product containing lactic acid.

Alcohol (e.g., ethanol), lactic acid, or the like produced using the methods of the present invention may be used as a material for producing food, pharmaceutical drugs, and various industrial products.

Hereinafter, the present invention will be described by way of examples, but the present invention is not limited to these examples.

EXAMPLES

Example 1; Preparation of Yeast Capable of Displaying α-Galactosidase on its Surface Layer A cDNA encoding *Aspergillus oryzae* α-galactosidase of AglC ("AOAglC") was obtained. In order to obtain this, PCR was performed using the genome DNA of *Aspergillus oryzae* as a template with a pair of primers having sequences of SEQ ID Nos. 3 and 4.

pAUR101 (manufactured by Takara Bio. Inc.) was used as a vector to be introduced into yeast. A surface-display cassette in which the *Saccharomyces cerevisiae* SED1 promoter (SEQ ID No. 5), a secretion signal (SEQ ID No. 6; its amino acid sequence is also shown in SEQ ID No. 7), the AOAglC (SEQ ID No. 8; its amino acid sequence is also shown in SEQ ID No. 9), the *Saccharomyces cerevisiae* SED1 anchor (SEQ ID No. 10; its amino acid sequence is also shown in SEQ ID No. 11), and the α-agglutinin terminator of *Saccharomyces cerevisiae* (SEQ ID No. 12) were arranged in the stated order was inserted into a SmaI cloning site of pAUR101 using an In-Fusion enzyme reaction. The obtained plasmid was named "pAUR101-SED1p-AOAglC-SED1-SAG1t".

This pAUR101-SED1p-AOAglC-SED1-SAG1t was cleaved using StuI and then used to transform the *Saccharomyces cerevisiae* TJ14 strain using YEAST MAKER yeast transformation system (Clontech Laboratories, Palo Alto, Calif., USA), and an Aureobasidin A-resistant strain was thus obtained Thus, yeast capable of displaying α-galactosidase on its surface layer was obtained.

Example 2: Evaluation of Properties of Yeast Capable of Displaying α-Galactosidase on its Surface Layer (2-1: Evaluation of α-Galactosidase Activity Using Synthetic Substrate, p-Nitrophenyl α-D-Galactopyranoside)

After the yeast capable of displaying α-galactosidase on its surface layer obtained in Example 1 (about 0.77 μg/L (wet weight base)) was reacted at 30° C. for 10 minutes in the presence of 1 mM of p-nitrophenyl α-D-galactopyranoside, the absorbance at 400 nm was measured, and the α-galactosidase titer (U/g) was calculated from the measured absorbance. As a result, the α-galactosidase activity of 300 to 800 U/g (wet cell weight) titer was detected. Accordingly, it was confirmed that the yeast could display α-galactosidase on its surface layer.

(2-2: Ethanol Fermentation Using Raffinose)

In a YP liquid culture medium containing 50 g/L raffinose (70 wt % raffinose and 30 wt % galactose) in a DURAN bottle, 20 g (wet weight)/L the yeast capable of displaying α-galactosidase on its surface layer obtained in Example 1 was cultured at 30° C. for 48 hours under stirring at 200 rpm using a stirrer bar. The culture medium was collected after 2 hours, 7 hours, 22 hours, 26 hours, and 48 hours, and the concentration of ethanol produced through fermentation and the concentration of residual raffinose were measured.

The results are shown in FIG. 1. The vertical axis indicates the concentrations (g/L) of ethanol and raffinose, and the horizontal axis indicates the culture time (hours). Symbols in this diagram are as follows: filled rhomboids indicate the ethanol concentrations for wild-type yeast (*Saccharomyces cerevisiae* TJ14 strain) ("EtOH-TJ"); filled squares indicate the ethanol concentrations for the surface-display yeast ("EtOH-TJ-AOAglC"); white rhomboids indicate the raffinose concentrations for wild-type yeast ("Raffinose-TJ"); and white squares indicate the raffinose concentrations for the surface-display yeast ("Raffinose-TJ-AOAglC"). In the case of the wild-type yeast, a decrease in the raffinose concentration was not observed during the culture, whereas in the case of the surface-display yeast, the raffinose concentration decreased to almost zero after 7 hours of culture. The ethanol production significantly increased in the case of the surface-display yeast compared with the case of the wild-type yeast. It was thought that the ethanol production observed also in the case of the wild-type yeast was due to glucose, galactose, or the like in the liquid culture medium.

(2-3: Ethanol Fermentation Using Stachyose)

The yeast capable of displaying α-galactosidase on its surface layer obtained in Example 1 (20 g/L) were cultured under the same conditions as those in 2-2 above, except that a YP liquid culture medium containing 50 g/L stachyose (65 wt % stachyose and 35 wt % other sugars (raffinose, sucrose, and galactose)) was used. The culture medium was collected after 2 hours, 7 hours, 22 hours, 26 hours, and 48 hours, and the concentration of ethanol produced through fermentation and the concentration of residual stachyose were measured.

Figure 2:
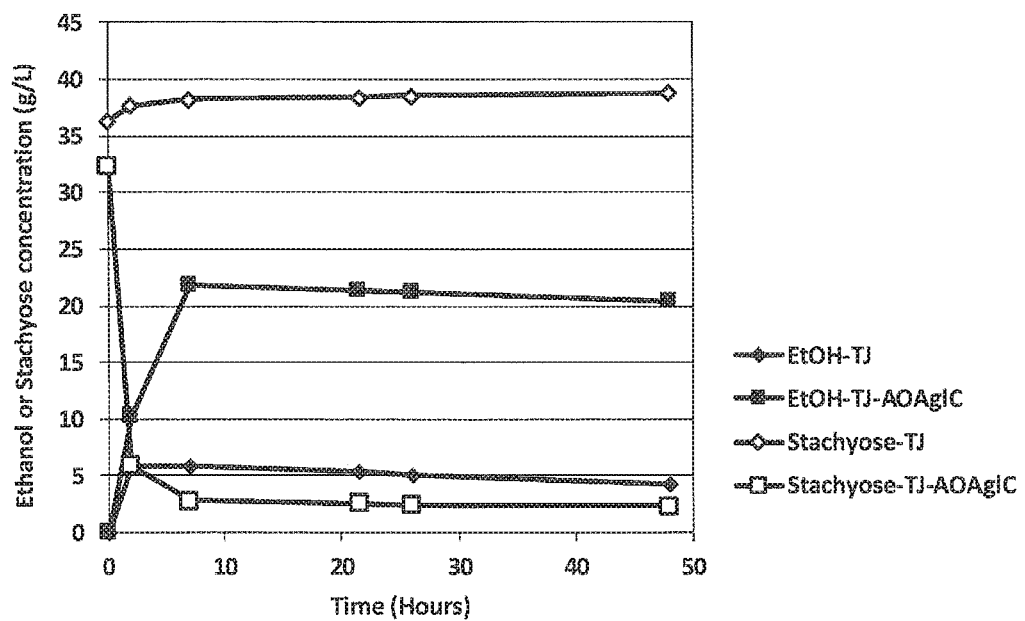
FIG. 2 is a graph showing the ethanol fermentation generated from culturing yeast capable of displaying α-galactosidase on its surface layer in a liquid culture medium containing stachyose.

The results are shown in FIG. 2. The vertical axis indicates the concentrations (g/L) of ethanol and stachyose, and the horizontal axis indicates the culture time (hours). Symbols in this diagram are as follows: filled rhomboids indicate the ethanol concentrations for wild-type yeast (*Saccharomyces cerevisiae* TJ14 strain) ("EtOH-TJ"); filled squares indicate the ethanol concentrations for the surface-display yeast ("EtOH-TJ-AOAglC"); white rhomboids indicate the stachyose concentrations for wild-type yeast ("Stachyose-TJ"); and white squares indicate the stachyose concentrations for the surface-display yeast ("Stachyose-TJ-AOAglC"). In the case of the wild-type yeast, a decrease in the stachyose concentration was not observed during the culture, whereas in the case of the surface-display yeast, the stachyose concentration had rapidly decreased by 7 hours after the start of culture. The ethanol production significantly increased in the case of the surface-display yeast compared with the case of the wild-type yeast. It was thought that the ethanol production observed also in the case of the wild-type yeast was due to glucose, fructose, sucrose, galactose, or the like in the liquid culture medium.

(2-4: Ethanol Fermentation Using Melibiose)

In a YP liquid culture medium containing 50 g/L melibiose in a DURAN bottle, 20 g (wet weight)/L the yeast capable of displaying α-galactosidase on its surface layer obtained in Example 1 was cultured at 30° C. for 48 hours under stirring at 200 rpm using a stirrer bar. The culture medium was collected after 2 hours, 7 hours, 22 hours, 26 hours, and 48 hours, and the concentration of ethanol produced through fermentation and the concentration of residual melibiose were measured.

Figure 3:
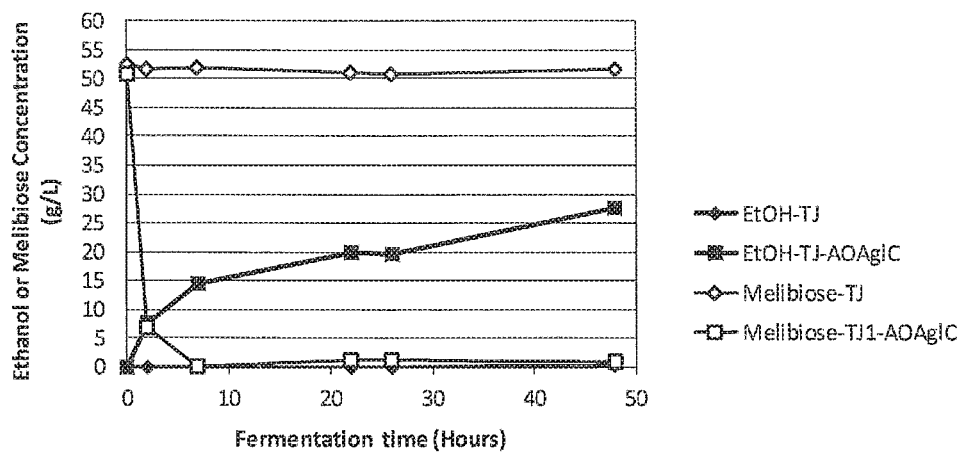
FIG. 3 is a graph showing the ethanol fermentation generated from culturing yeast capable of displaying α-galactosidase on its surface layer in a liquid culture medium containing melibiose.

The results are shown in FIG. 3. The vertical axis indicates the concentrations (g/L) of ethanol and melibiose, and the horizontal axis indicates the culture time (hours). Symbols in this diagram are as follows: filled rhomboids indicate the ethanol concentrations for wild-type yeast (*Saccharomyces cerevisiae* TJ14 strain) ("EtOH-TJ"); filled squares indicate the ethanol concentrations for the surface-display yeast ("EtOH-TJ-AOAglC"); white rhomboids indicate the melibiose concentrations for wild-type yeast ("Melibiose-TJ"); and white squares indicate the melibiose concentrations for the surface-display yeast ("Melibiose-TJ-AOAglC"). In the case of the wild-type yeast, a decrease in the melibiose concentration was not observed during the culture, whereas in the case of the surface-display yeast, the melibiose concentration decreased to about zero after 7 hours of culture. The ethanol production significantly increased in the case of the surface-display yeast compared with the case of the wild-type yeast.

Example 3: Ethanol Fermentation Using Soybean Molasses

In a YP liquid culture medium containing 800 g/L soybean molasses in a DURAN bottle, 20 g (wet weight)/L the yeast capable of displaying α-galactosidase on its surface layer obtained in Example 1 or wild-type yeast (*Saccharomyces cerevisiae* TJ14 strain) was cultured at 35° C. for 96 hours under stirring at 200 rpm using a stirrer bar. The culture medium was collected after 2 hours, 7 hours, 22 hours, 26 hours, 48 hours, 72 hours, and 96 hours, and the concentration of ethanol produced through fermentation and the concentrations of residual raffinose and stachyose were measured using HPLC.

Figure 4:
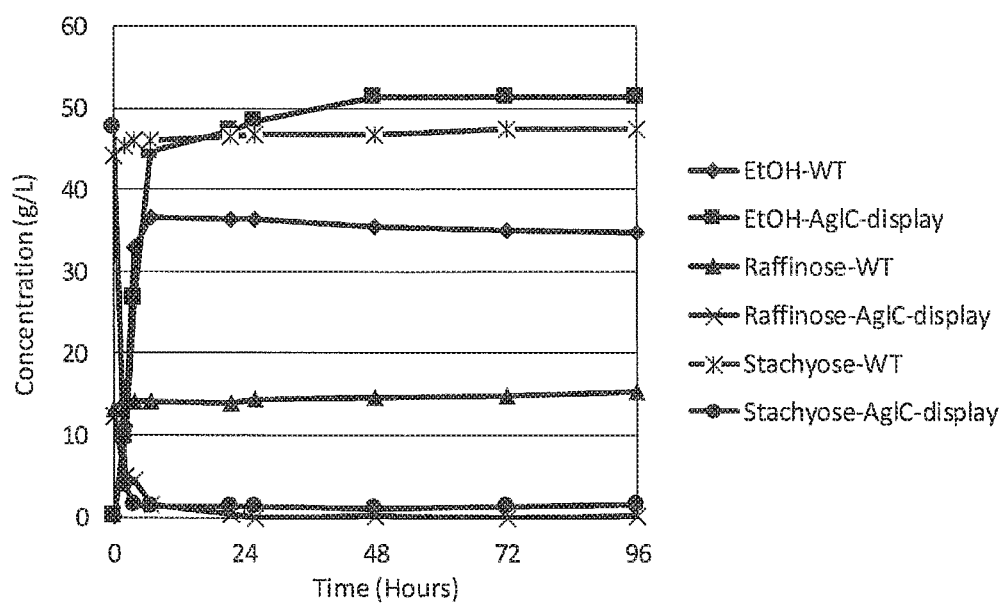
FIG. 4 is a graph showing the ethanol fermentation generated from culturing yeast capable of displaying α-galactosidase on its surface layer in a liquid culture medium containing soybean molasses.

The results are shown in FIG. 4. The vertical axis indicates the concentrations (g/L) of ethanol, raffinose, and stachyose, and the horizontal axis indicates the culture time (hours). Symbols in this diagram are as follows; filled rhomboids indicate the ethanol concentrations for the wild-type yeast ("EtOH-WT"); filled squares indicate the ethanol concentrations for the surface-display yeast ("EtOH-AglC-Display"); filled triangles indicate the raffinose concentrations for the wild-type yeast ("Raffinose-WT"); crosses indicate the raffinose concentrations for the surface-display yeast ("Raffinose-AglC-Display"); asterisks indicate the stachyose concentrations for the wild-type yeast ("Stachyose-WT"); and filled circles indicate the stachyose concentrations for the surface-display yeast ("Stachyose-AglC-Display"). In the case of the wild-type yeast, decreases in the raffinose concentration and the stachyose concentration were not observed during the culture, whereas in the case of the surface-display yeast, the raffinose concentration and the stachyose concentration had rapidly decreased by 7 hours after the start of the culture. Although ethanol was also produced in the case of the wild-type yeast (this may be due to sugars (e.g., sucrose) other than raffinose and stachyose in the soybean molasses), the amount of the produced ethanol significantly increased in the case of the surface-display yeast compared with the case of the wild-type yeast.

Example 4: Evaluation of Thermal Stability of α-Galactosidase Displayed on Surface Layer of Yeast (4-1: Evaluation of Thermal Stability of α-Galactosidase Activity Using Synthetic Substrate, p-Nitrophenyl α-D-Galactopyranoside)

In the reaction with the synthetic substrate described in "2-1" of Example 2 above, the yeast capable of displaying α-galactosidase on its surface layer obtained in Example 1 (about 0.77 μg/L (wet weight base)) were incubated at 50° C. for 168 hours in the presence of 1 mM p-nitrophenyl α-D-galactopyranoside, and a change in the α-galactosidase activity was examined.

Figure 5:
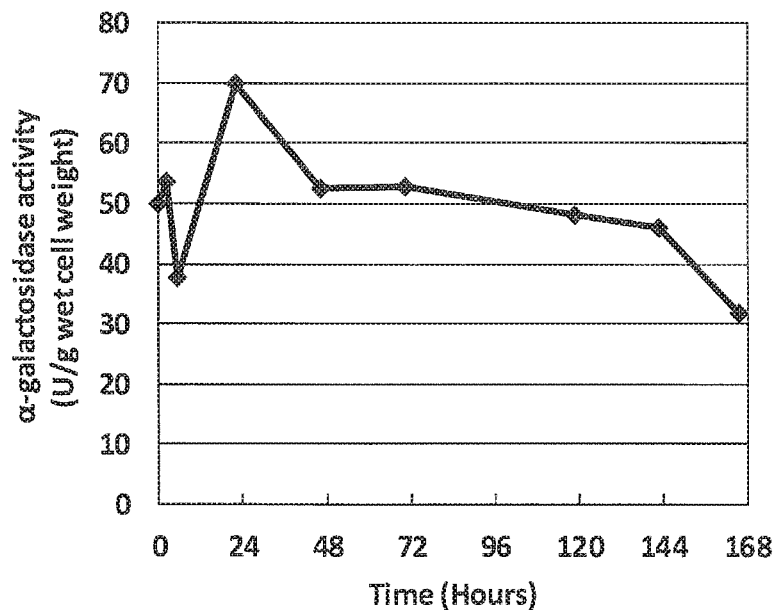
FIG. 5 is a graph showing a time-dependent variation in activity of α-galactosidase displayed on the surface layer of yeast at 50° C.

The results are shown in FIG. 5. The vertical axis indicates the α-galactosidase activity (U/g wet cell weight), and the horizontal axis indicates the incubation time (hours). Filled rhomboids indicate the results of the measurement of the α-galactosidase activity. It is clear from the results that the activity temporarily increased during the treatment and then slowly decreased, but was maintained until 120 hours elapsed. Accordingly, although yeast metabolizing (i.e., production of ethanol through fermentation) was not generated under high temperature such as 50° C., the activity of the α-galactosidase displayed on the surface layer of the yeast was still maintained.

(4-2: Evaluation of Glycolysis in High-Temperature Batch Culture Using Soybean Molasses)

The yeast capable of displaying α-galactosidase on its surface layer obtained in Example 1 was cultured in 100 mL of a YPD culture medium (in a 300 mL Erlenmeyer flask) at 30° C. at 150 rpm for 3 days. Next, the yeast was collected (at 3500 rpm for 5 minutes) and washed once with water, and then the concentration thereof was adjusted to 200 g (wet weight)/L with water. Subsequently, the yeast was incubated in a rotary incubator at 50° C. for 2 hours. Thereafter, soybean molasses, the yeast (200 g (wet weight)/

L), and water were mixed at a weight ratio of 500:100:400 (the final concentrations of the soybean molasses and the yeast were respectively 500 g/L and 20 g (wet weight)/L) and sampled ("0 h" of "1st"), and the mixture was further incubated (subjected to heat treatment) in the rotary incubator at 50° C. for 2 hours and then sampled ("2 h" of "1st"). The solution containing the soybean molasses subjected to the heat treatment was centrifuged at 3500 rpm for 5 minutes, and the yeast was collected by removing the supernatant. Fresh soybean molasses and water were added to the yeast such that the concentration of the soybean molasses was 500 g/L, and the mixture was sampled ("0 h" of "2nd"). Then, the mixture was further incubated (subjected to heat treatment) in the rotary incubator at 50° C. for 2 hours and then sampled ("2 h" of "2nd"). The total sugar concentrations of monosaccharides and sucrose in the respective samples obtained through sampling were quantified using HPLC.

Figure 6:
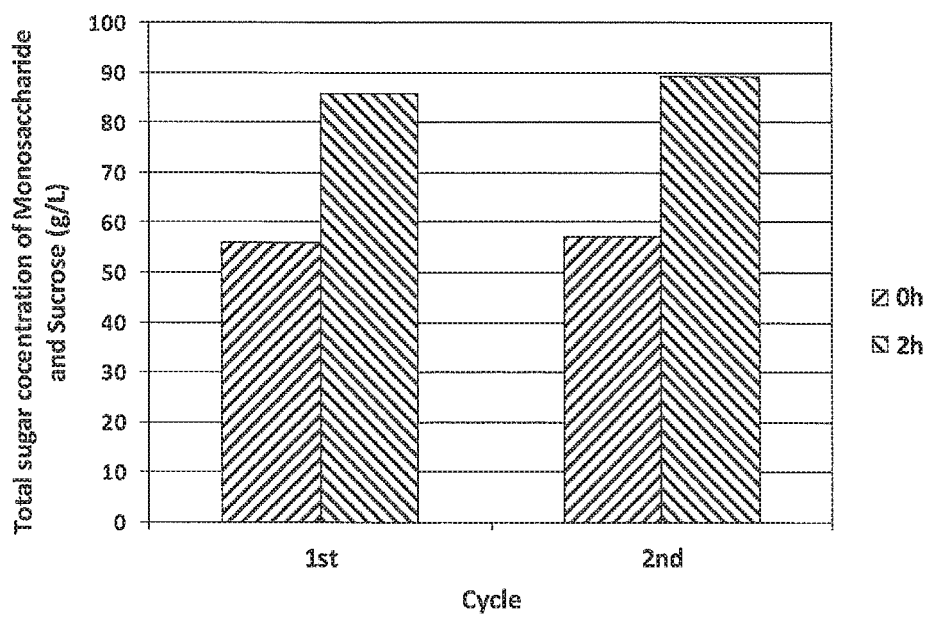
FIG. 6 is a graph showing the total sugar concentrations of monosaccharides and sucrose before and after 2-hour incubation of yeast capable of displaying galactosidase on its surface layer with soybean molasses at 50° C., the incubation being repeatedly performed.

The results are shown in FIG. 6. The vertical axis indicates the total sugar concentration (g/L) of monosaccharides and sucrose, and the horizontal axis indicates the cycle ("1st" and "2nd"). In FIG. 6, regarding the results from both of the first time ("1st") and the second time ("2nd"), the result from the sampling ("0 h") performed immediately after the yeast and the soybean molasses were added and mixed is shown on the left side, and the result from the sampling ("2 h") performed after the mixture had been incubated at 50° C. for 2 hours is shown on the right side. In both the first time and the second time, an increase in the total sugar concentration of monosaccharides and sucrose was observed after the 2-hour long incubation at 50° C. This suggests that, under high temperature such as 50° C., the α-galactosidase displayed on the surface layer of yeast hydrolyzes oligosaccharides, such as raffinose and stachyose, which contain α-1,6 linked galactose, in the soybean molasses to produce sugars having a smaller number of saccharides (e.g., monosaccharides and sucrose), and the yeast does not use the thus-produced sugars for the fermentation.

It was found from the results of 4-1 and 4-2 above that although yeast metabolizing (i.e., production of ethanol through fermentation) was not generated under high temperature such as 50° C., the activity of the α-galactosidase displayed on the surface layer of the yeast was still maintained.

Example 5: Evaluation of Properties of Lyophilized Surface Display of α-Galactosidase The yeast capable of displaying α-galactosidase on its surface layer obtained in Example 1 was lyophilized at 50° C. for 3 hours. The lyophilized yeast capable of displaying α-galactosidase on its surface layer is also referred to as "lyophilized surface-display yeast" hereinafter.

(5-1: Evaluation of α-Galactosidase Activity Using Synthetic Substrate, p-Nitrophenyl α-D-Galactopyranoside)

After the lyophilized surface-display yeast was reacted at 30° C. or 50° C. for 10 minutes in the presence of 1 mM of a synthetic substrate, p-nitrophenyl α-D-galactopyranoside, the absorbance at 400 nm was measured, and the α-galactosidase titer (U/g) was calculated from the measured absorbance. Table 1 shows the results.

TABLE 1

| Reaction Temperature (° C.) | Titer (U/g (Lyophilized yeast)) |
|---|---|
| 30 | 1589.5 |
| 50 | 3225.6 |

(5-2: Evaluation of Glycolysis at High Temperature Using Soybean Molasses)

Under shaking at 500 rpm, the lyophilized surface-display yeast at 4 g (dry weight)/L was reacted with soybean molasses (suspended in water at a concentration of 90 wt %) at 50° C. for 2 hours. The reaction solution was collected as appropriate, and the concentrations of stachyose, raffinose, and galactose were measured using HPLC. It should be noted that the galactose level is measured as including fructose and the like under this measurement condition, and was thus calculated as a deemed galactose level.

Figure 7:
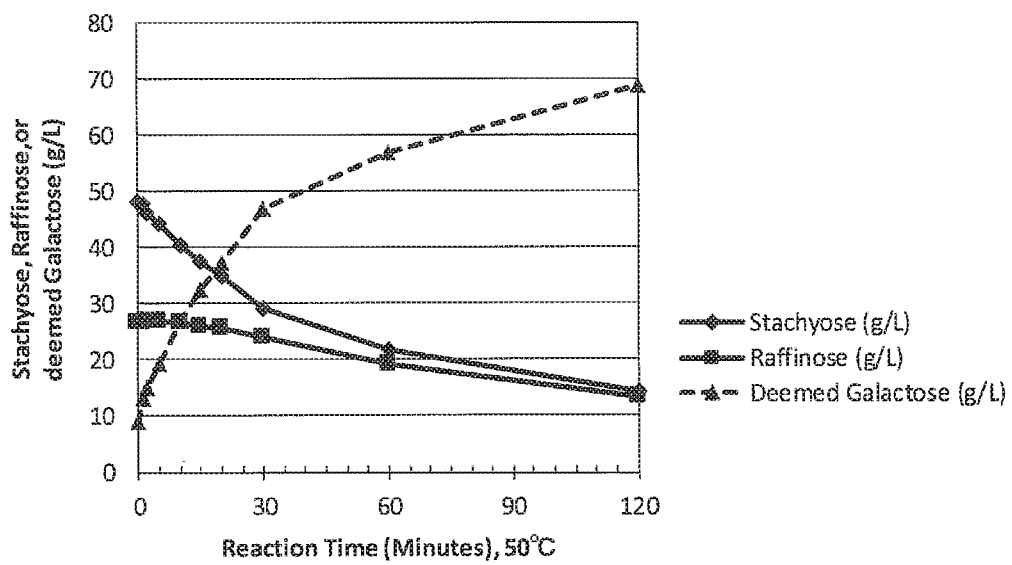
FIG. 7 is a graph showing changes in a stachyose level, a raffinose level, and a deemed galactose level when lyophilized surface-display yeast was combined with soybean molasses in a liquid culture medium at 50° C.

The results are shown in FIG. 7. The vertical axis indicates the concentrations (g/L) of stachyose, raffinose, and deemed galactose, and the horizontal axis indicates the reaction time (hours) for incubation. Symbols in this diagram are as follows: filled rhomboids indicate the stachyose concentrations (g/L); filled squares indicate the raffinose concentrations (g/L); and filled triangles indicate the deemed galactose concentrations (g/L). As the reaction time elapsed, the stachyose concentration and the raffinose concentration decreased, and an increase in the galactose concentration was observed. The titer for the soybean molasses cannot be calculated merely from the amount of decreases in stachyose and raffinose for the reasons as shown the followings: galactose cannot be precisely quantified; stachyose contains two galactose molecules; and raffinose may be produced due to degradation of stachyose. Accordingly, the minimum activity value of α-galactosidase was calculated from only the amount of a decrease in stachyose was 432.8 U/g (10 minutes after the start of the reaction), and the maximum value thereof was 1018.3 U/g (2 minutes after the start of the reaction). Just for reference, the activity value calculated from the galactose level was 3720.6 U/g (10 minutes after the start of the reaction), which suggests that this value is close to the activity value for the synthetic substrate in consideration of the fructose level, and therefore, the lyophilized surface-display yeast sufficiently acts on a raw material.

Example 6: Lactic Fermentation Using Soybean Molasses

The yeast capable of displaying α-galactosidase on its surface layer obtained in Example 1 was incubated in a rotary incubator at 50° C. for 2 hours and thus subjected to heat treatment. Under shaking at 500 rpm, 500 g of water containing 20 g (wet weight) of the surface-display yeast after heat treatment and 500 g of soybean molasses were reacted with each other at 50° C. for 2 hours. After this reaction, such obtained soybean molasses was used for subsequent culture of lactic acid bacterium. Specifically, the soybean molasses after the reaction at 250 g/L and lactic acid bacterium (*Lactobacillus plantarum* WCFS1 strain (Kleerebezem et al., PNAS, 2003, Vol. 100, p. 1990-1995): this strain is the same as NCIMB8826 (Okano et al., Appl. Environ. Microbiol., 2009, Vol. 75, p. 462-467)) at 40 g (wet weight)/L were mixed with an MRS culture medium in a flask, and the lactic acid bacterium was cultured at 37° C. for 25 hours under stirring at 200 rpm using a stirrer bar. In the case where the pH was regulated to 6 only at the start of the culture and in the case where the pH was regulated to be constant at 6 throughout the culture, the culture solution was collected at the start of the culture and after 3 hours, 18 hours, and 25 hours, and the concentrations of lactic acid and sugars (monosaccharides and disaccharides: including fructose, galactose, glucose, and sucrose) in the solution were measured using HPLC. The concentration of lactic acid produced by the lactic acid bacterium during the culture (produced lactic acid) was determined by subtracting the concentration of lactic acid measured at the start (0 hours after the start of the culture) (this may be due to lactic acid that naturally occurs in the soybean molasses) from the concentration of lactic acid measured at each collection.

Figure 8:
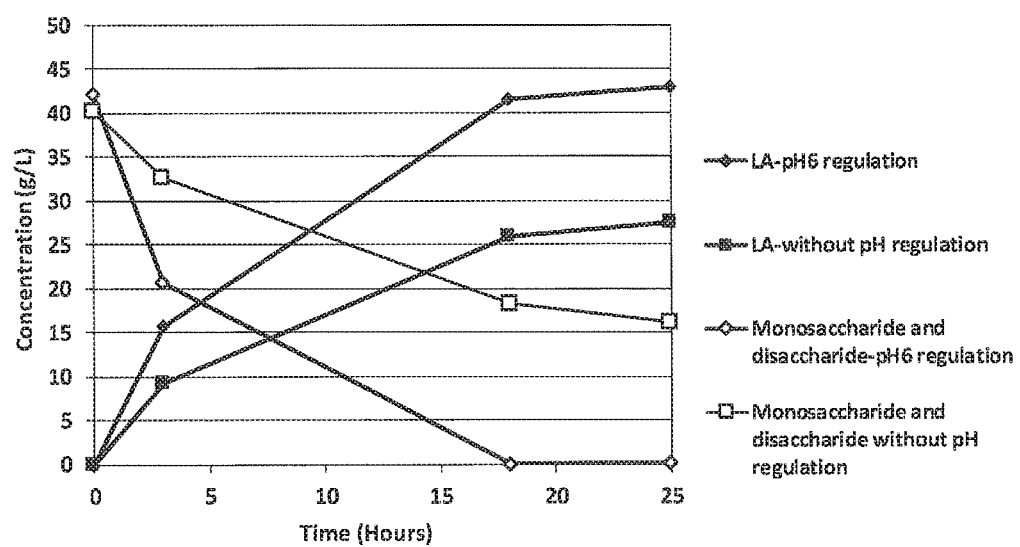
FIG. 8 is a graph showing the lactic fermentation generated in a reaction solution containing a lactic acid bacterium and a material obtained after combining soybean molasses with heat-treated surface-display yeast.

The results are shown in FIG. 8. The vertical axis indicates the concentrations (g/L) of the produced lactic acid as well as monosaccharides and disaccharides, and the horizontal axis indicates the time (hours) for the culture of lactic acid bacterium. Symbols in this diagram are as follows: filled rhomboids indicate the lactic acid concentrations (g/L) with pH 6 regulation; filled squares indicate the lactic acid concentrations (g/L) without pH regulation; white rhomboids indicate the sugar concentrations (g/L) with pH 6 regulation; and white squares indicate the sugar concentrations (g/L) without pH regulation. With or without the pH regulation, the lactic acid concentration increased and the sugar concentration decreased as the time elapsed, and lactic fermentation by the lactic acid bacterium was observed. In particular, in the case where the pH was regulated to be 6 throughout the culture (fermentation reaction), it was observed that a large amount of lactic acid was obtained through fermentation, and yield of fermentation reached 100%.

Example 7: Saccharification of Soybean Molasses and Lactic Fermentation

Under shaking at 500 rpm, 500 g of water containing 20 g (wet weight) of the yeast capable of displaying α-galactosidase on its surface layer subjected to heat treatment in the same manner as in Example 6, and 500 g of soybean molasses were reacted with each other at 50° C. for 2 hours. Table 2 below shows the sugar concentrations in the soybean molasses before and after this reaction. It should be noted that the total amount of reaction solution was 1 kg after the reaction, and therefore, Table 2 also shows the sugar concentrations that are converted as being in 500 g of the reaction solution, likely before the reaction.

Furthermore, 500 g of the solution containing the soybean molasses was collected after the above-mentioned reaction and used for the culture of lactic acid bacterium. Specifically, 500 g of the solution and 500 g of an MRS culture medium containing 5 g (wet weight) of lactic acid bacterium (Lactobacillus plantarum WCFS1 strain) were mixed together, and the lactic acid bacterium was cultured at 37° C. for 1 day under shaking at 200 rpm to generate a fermentation. The pH was regulated to be constant at 6 throughout the fermentation period. Table 2 below shows the concentrations of lactic acid and sugars in the solution before and after fermentation.

TABLE 2

| | Concentration in Reaction Solution (g/L) | | | Concentration in Fermentation Solution (g/L) | |
|---|---|---|---|---|---|
| | Before Reaction | After Reaction | (Converted Amount) | Before Fermentation | After Fermentation |
| Raffinose | 16.6 | 0.4 | 0.8 | 0.4 | 0 |
| Stachyose | 51.8 | 1.2 | 2.4 | 1.2 | 0.4 |
| Sucrose | 87.6 | 61.1 | 122.2 | 61.1 | 0 |
| Fructose | 12.6 | 6.3 | 12.6 | 6.3 | 0 |
| Galactose | 0 | 14.8 | 29.6 | 14.8 | 0 |
| Glucose | 0 | 0 | 0 | 0 | 0 |
| Total Sugars | 168.7 | 83.7 | 167.4 | 83.7 | 0.4 |
| Lactic Acid | — | — | — | — | 39.4 |
| Amount of Solution (g) | 500 g | 1000 g | 500 g | 500 g | 1000 g |

As shown in Table 2, it was observed that, due to the reaction with the surface-display yeast, the amounts of raffinose and stachyose decreased and the amounts of sucrose and galactose increased in the soybean molasses. This suggests that the surface-display yeast hydrolyzed and saccharified raffinose and stachyose into sucrose and galactose. Furthermore, it was observed that the saccharified soybean molasses was used by the lactic acid bacterium to produce a lactic fermentation.

Example 8: Preparation of Lactic Acid Bacterium Capable of Displaying α-Galactosidase As a host, Laycillus plantarum WCFS1 strain, which produces L- and D-lactic acid, was used. An artificial synthetic gene of α-galactosidase C derived from Aspergillus oryzae ("AOAglC for Lac" (SEQ ID No. 13; SEQ ID No. 14 indicates its amino acid sequence)) that was subjected to codon optimization for the host was used as a gene for introduction.

A plasmid (pCUA) was prepared by inserting the gene of the PgsA anchor (a subunit of a poly-γ-glutamic acid biosynthesis enzyme complex, PgsBCA, derived from Baccilus subtilis) between the NdeI site and the BamHI site in a pCU plasmid (Okano et al., Appl Microbiol Biotechnol, 2007, Vol. 75, p. 1007-1013), and the artificial synthetic codon-optimized α-galactosidase gene was inserted between the BamHI site and the HindIII site in the pCUA to prepare a plasmid, pCUA-AOAglC for Lac.

This plasmid, pCUA-AOAglC for Lac, was used in an electroporation method to transform the Lactobacillus plantarum WCFS1 strain, and colonies of the transformant were obtained on an MRS culture medium containing 5 μg/mL erythromycin. A portion of these colonies was subjected to PCR with a primer pair of pgsA-Cter-Fw (SEQ ID No. 15) and AOAglC for lac-Cter-Rv (SEQ ID No. 16). A band was clearly observed at the size of 2159 bp, and it was thus determined that the transformant had the introduced gene.

Example 9: Evaluation of Properties of Lactic Acid Bacterium Capable of Displaying α-Galactosidase on its Surface Layer (9-1: Evaluation of α-Galactosidase Activity Using Synthetic Substrate, p-Nitrophenyl α-D-Galactopyranoside)

After the lactic acid bacterium capable of displaying α-galactosidase on its surface layer obtained in Example 8 was cultured on an MRS plate culture medium (supplemented with 5 μg/mL erythromycin and 1% (w/v) calcium carbonate) at 37° C. for 2 days, the bacterial cells were scraped off using a platinum loop and the amount thereof was measured. Then, 100 μL of water was added thereto, and the mixture was agitated using a vortex mixer. A bacterial cell suspension was thus obtained. After 30 μL of the bacterial cell suspension was reacted at 30° C. for 20 minutes in the presence of 1 mM of p-nitrophenyl α-D-galactopyranoside, the absorbance at 400 nm was measured, and the α-galactosidase activity (U/g) was calculated from the measured absorbance. As a result, the α-galactosidase activity of 0.29 to 0.69 U/g (wet cell weight) was detected although it varied for the colonies. Accordingly, it was confirmed that the lactic acid bacterium displayed α-galactosidase on its surface layer.

(9-2: Lactic Fermentation Using Raffinose)

One cell line (#11) of the lactic acid bacterium capable of displaying α-galactosidase on its surface layer obtained in Example 8 was cultured by placing 5 mL of a YP liquid culture medium containing 2 (w/v) % raffinose, 1 (w/v) % calcium carbonate, and 5 (w/v) % a preculture bacterial suspension (obtained by culturing the ell line in a YP liquid culture medium containing 0.5 (w/v) % glucose for 1 day) in a test tube and allowing it to stand at 37° C. for 24 hours.

Figure 9:
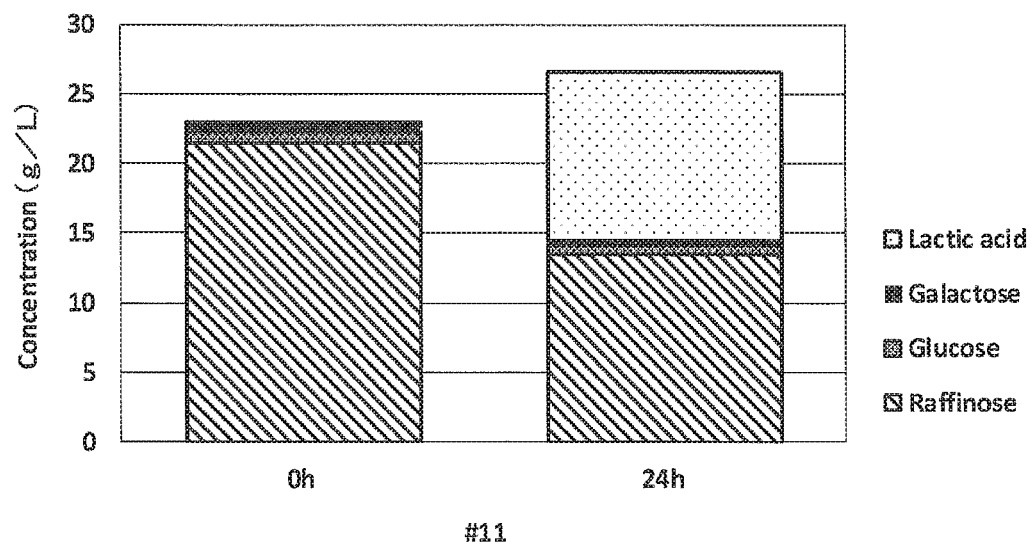
FIG. 9 is a graph showing the results of lactic fermentation generated from culturing a lactic acid bacterium capable of displaying α-galactosidase on its surface layer in a liquid culture medium containing raffinose.

The results are shown in FIG. 9. The vertical axis indicates the concentrations (g/L) of the components in a culture solution, and the horizontal axis indicates the culture starting time ("0 h") and the culture finishing time ("24 h"). In each of the bars in the bar graph for 0 hours and 24 hours, areas corresponding to the concentrations of raffinose, glucose, galactose, and lactic acid are stacked in this order from the bottom. After 24 hours, the concentration of raffinose had decreased and the concentration of lactic acid had increased. Since *Lactobacillus plantarum* also utilizes galactose, the accumulation of galactose was not observed in the culture medium.

Example 10: Lactic Fermentation Using Soybean Molasses

One cell line (WCSF1 #1121-1) of the lactic acid bacterium capable of displaying α-galactosidase on their surface layers obtained in Example 8 was cultured by placing 50 mL of a culture solution containing 20 (w/v) % soybean molasses, 2 (w/v) % calcium carbonate, and 5 (w/v) % a preculture bacterial suspension (obtained by culturing the cell line in a YP liquid culture medium containing 0.5 (w/v) % glucose for 1 day) in a DURAN bottle and stirring the culture solution at 200 rpm using a stirrer bar at 37° C. for 72 hours. The culture medium was collected after 18 hours, 24 hours, 48 hours, and 72 hours, and the concentration of lactic acid in the culture medium was measured using HPLC. The concentration of lactic acid produced by the lactic acid bacterium during the culture (produced lactic acid) was determined by subtracting the concentration of lactic acid measured at the start (0 hours after the start of the culture) (this may be due to lactic acid produced during the preculture and lactic acid that naturally occurs in the soybean molasses) from the concentration of lactic acid measured at each collection.

Figure 10:
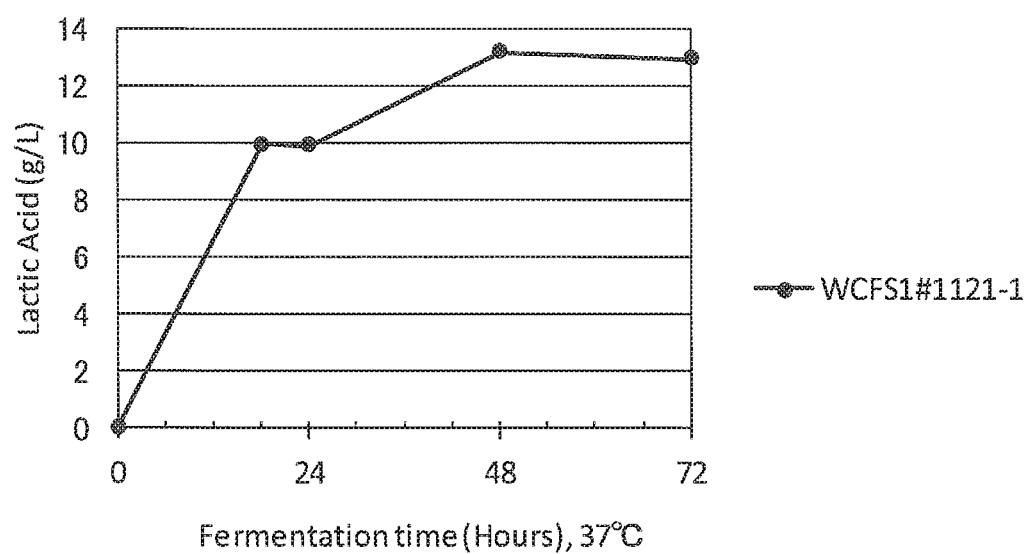
FIG. 10 is a graph showing the results of lactic fermentation generated from culturing a lactic acid bacterium capable of displaying α-galactosidase on its surface layer in a liquid culture medium containing soybean molasses.

The results are shown in FIG. 10. The vertical axis indicates the concentration (g/L) of lactic acid, and the horizontal axis indicates the time of culture (hours). Filled circles indicate the results of the concentration of lactic acid. It was confirmed that the lactic acid bacterium capable of displaying α-galactosidase on its surface layer also produced lactic acid over time in the culture medium containing soybean molasses.

INDUSTRIAL APPLICABILITY

According to the present invention, soybean molasses, which has conventionally been discarded, can be effectively utilized as a sugar raw material. Therefore, the present invention is useful for producing food, pharmaceutical drugs, and various industrial products using alcohol (e.g., ethanol), lactic acid, or the like as a raw material.

The invention claimed is:

1. A transformed microorganism capable of displaying α-galactosidase on its surface layer, wherein the α-galactosidase is α-galactosidase C (AglC) obtained from *Aspergillus oryzae*, and wherein a host of the microorganism is a yeast or lactic acid bacterium.

2. The transformed microorganism according to claim 1, wherein the microorganism has an alcohol fermentation ability.

3. The transformed microorganism according to claim 1, wherein the yeast belongs to the genus *Saccharomyces, Pichia, Schizosaccharomyces, Kluyveromyces*, or *Candida*.

4. The transformed microorganism according to claim 3, wherein the yeast is *Saccharomyces cerevisiae*.

5. The transformed microorganism according to claim 1, which is an inactivated microorganism.

6. An α-galactosidase enzyme agent comprising the transformed microorganism according to claim 1.

7. A method for producing alcohol, comprising:
a step of culturing the transformed microorganism according to claim 2 in a culture medium containing a material that contains an oligosaccharide containing α-1,6 linked α-galactose.

8. The method according to claim 7, wherein the alcohol is ethanol.

9. A method for saccharifying a material that contains an oligosaccharide containing α-1,6 linked α-galactose, the method comprising:
a step of combining the transformed microorganism according to claim 1 or the α-galactosidase enzyme agent with the material that contains the oligosaccharide containing α-1,6 linked α-galactose.

10. A method for producing lactic acid, comprising:
a step of obtaining a saccharified material by combining the transformed microorganism according to claim 1 or the α-galactosidase enzyme agent with a material that contains an oligosaccharide containing α-1,6 linked α-galactose, and
a step of culturing a lactic acid bacterium in a culture medium containing the saccharified material.

11. A method for producing lactic acid, comprising:
a step of culturing the transformed microorganism according to claim 1 in a culture medium containing a material that contains an oligosaccharide containing α-1,6 linked α-galactose.

12. The method according to claim 7, wherein the oligosaccharide containing α-1,6 linked α-galactose includes at least one sugar of raffinose, stachyose, melibiose, and verbascose.

* * * * *